(12) United States Patent
Hoffmann et al.

(10) Patent No.: US 8,097,463 B2
(45) Date of Patent: Jan. 17, 2012

(54) USE OF ARYLBORONIC ACIDS IN PROTEIN LABELLING

(75) Inventors: Ralf Hoffmann, Brueggen (DE); Helga Hummel, Aachen (DE); Volker Weiler, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 227 days.

(21) Appl. No.: 12/513,403

(22) PCT Filed: Oct. 26, 2007

(86) PCT No.: PCT/IB2007/054354
§ 371 (c)(1),
(2), (4) Date: May 4, 2009

(87) PCT Pub. No.: WO2008/056290
PCT Pub. Date: May 15, 2008

(65) Prior Publication Data
US 2010/0041162 A1    Feb. 18, 2010

(30) Foreign Application Priority Data
Nov. 6, 2006    (EP) .................................. 06123496

(51) Int. Cl.
*C07F 5/02*    (2006.01)
(52) U.S. Cl. .................... 436/86; 568/1; 436/56
(58) Field of Classification Search .............. 436/86, 436/56; 568/1
See application file for complete search history.

(56) References Cited

U.S. PATENT DOCUMENTS 6,852,544 B2    2/2005    Aebersold et al.

FOREIGN PATENT DOCUMENTS

| WO | 02099077 A2 | 12/2002 |
| WO | 03008547 A2 | 1/2003 |
| WO | WO03/008547 | * 1/2003 |
| WO | 2004070352 A2 | 8/2004 |
| WO | 2006064451 A2 | 6/2006 |

OTHER PUBLICATIONS

Schnolzer et al: "Protease-Catalyzed Incorporation of 18O Into Peptide Fragments and Its Application for Protein Sequencing by Electrospray and Matrix-Assisted Laser Desorption/Ionization Mass Spectrometry"; Electrophoresis, 1996,, vol. 17, pp. 945-953.

Heller et al: "Trypsin Catalyzed 16O-to_18O Exchange for Comparative Proteomics: Tandem Mass Spectrometry Comparison Using MALDI-TOF, ESI-QTOP, and ESI-ION Trap Mass Spectrometers"; Journal of the American Society for Mass Spectrometry, 2003, vol. 14 (7), pp. 704-718.

Krokhin et al: "An Improved Model for Prediction of Retention Times of Tryptic Peptides in Ion Pair Reversed-Phase HPLC"; Molecular & Cellular Proteomics 3.9, 2004, pp. 908-919.

(Continued)

*Primary Examiner* — Jill Warden
*Assistant Examiner* — Monique Cole

(57) ABSTRACT

Tagging of Histidine in polypeptides with arylboronic acid tagging reagents for identifying proteins in a sample by isolating and identifying Histidine-comprising peptides from one protein sample or a pool of protein samples. Databases of Histidine-including peptides from in silico cleaved proteins are uses in the identification of proteins.

18 Claims, 9 Drawing Sheets

OTHER PUBLICATIONS

Bull et al: "Surface Tension of Amino Acid Solutions: A Hydrophobicity Scale of the Amino Acid Residues"; Archives of Biochemistry and Biophysics, 1974, vol. 161, pp. 665-670.

Collman et al: "Catalytic Activities of Cu(II) Complexes With Nitrogen-Chelating Bidentate Ligands in the Coupling of Imidazoles With Arylboronic Acids"; Journal of Organic Chemistry, 2001, vol. 66, pp. 7892-7897.

Collman et al: "The [Cu(OH)-TMEDA]2CL2-Catalyzed Coupling of Arylboronic Acids With Imidazoles in Water"; Journal of Organic Chemistry. 2001, vol. 66, pp. 1528-1531.

Mirzaei et al: "Structure Specific Chromatographic Selection in Targeted Proteomics"; Journal of Chromatography B:Biomedical Sciences & Application, vol. 817, No. 1, pp. 3-34.

* cited by examiner

USE OF ARYLBORONIC ACIDS IN PROTEIN LABELLING

FIELD OF THE INVENTION

The present invention relates to methods for the simultaneous analysis of protein samples using Mass spectrometry, allowing the selective isolation of peptides from a mixture of cleaved proteins. The present invention further relates to techniques for purifying peptides and data analysis of Mass spectrometry data.

BACKGROUND OF THE INVENTION

For the analysis of a complex protein sample (a tissue sample or a body fluid like serum, or urine) by proteomic methods, the sample is generally cleaved into peptides, the peptides are separated and analysed by Mass Spectrometry. The biggest problem to be overcome in such a "shotgun" approach is the reduction in complexity of the mixture of cleaved peptides. By digesting the proteins with proteases in order to provide fragments suitable for the analysis by currently used mass spectrometry instrumentation (optimal analysis range of these machines is in the order of 2000-4000 m/z), the number of molecules to be analysed is dramatically increased compared to the original sample. As different peptides in the mixture originate from the same parent protein upon cleavage, the analysis of all of these peptides may in some cases be redundant. On the other hand, the analysis of several peptides corresponding to the same protein can serve as a further confirmation in the identification of the parent protein.

In some analyses however, it is not necessary that all peptides originating from a protein are analysed. One or a few peptides are often sufficient to identify the presence of a certain protein in a sample. To reduce the number of peptides after cleavage, different functional groups of amino acids have been used to selectively isolate or label specific peptides. Functional groups which have been described as suitable for this purpose are the thiol group of Cysteine, the carboxyl group of Aspartic acid, Glutamic acid and the carboxyterminus, the amine groups of Lysine and the aminoterminus of peptides themselves.

Cysteine is often used as functional group in proteomics for the selective isolation or labelling of peptides. It occurs in about 85% of all proteins and on average occurs with a frequency of about 2 to 3% within a polypeptide. Accordingly, analysis of only the cysteine-comprising peptides of a protein sample have been considered as adequately representative of the entire protein pool. Furthermore, the thiol group of Cysteine does not occur in any other amino acid, allowing specific tagging or labelling. One disadvantage however is that Cysteine residues within a protein often form disulfide bridges, which contribute to the tertiary or quaternary structure of a protein and thus are often present in pairs. The use of Cysteine for the labelling of peptides will thus often label at least two peptides from the same protein, resulting in the generation of redundant information. Moreover, Cysteine residues are often located in domains of a protein which contribute to the structure of the protein. Such domains are often conserved between proteins with different function. Accordingly, unequivocal identification of a protein based on a Cysteine-comprising peptide thereof may be difficult. A further disadvantage of Cysteine is that, though the occurrence of Cysteine in proteins is relatively high, its distribution is somewhat uneven. While numerous Cysteine-rich proteins exist, not all proteins contain Cysteine (e.g. ribosomal proteins). Thus some proteins will be overlooked by Cysteine-directed tagging or labelling while others will be excessively represented. Finally, during manipulation of a sample, Cysteine residues may become oxidised. Such oxidised amino acids can no longer be used for thiol-specific tagging or labelling.

The imidazole group of Histidine, another unique functional group in proteins, is widely used for affinity chromatography, based on its inherent affinity for metal, but has been rarely used as a target for protein modification.

Histidine-tagged biomolecules, typically comprising a tail of 6 Histidine residues are purified by immobilised metal ion affinity chromatography (IMAC). Proteins with an artificially added or naturally occurring sequence comprising multiple Histidines, Cysteines or Tryptophanes in the correct configuration can be bound to a column matrix containing covalently bound chelated metal ions. Most commonly, Ni chelate chromatography is used as a matrix in affinity chromatography to purify recombinant proteins that have been expressed as fusion proteins with one or more $His_6$ tags at the N- or C-terminus of the protein. Typically, the nickel ions are attached to the column matrix via nitrilotriacetate groups and interact with Histidine residues in the tagged protein in exchange for water. Elution is brought about either using a gradient of increasing imidazole concentration, or in stepwise procedure. Apart from $Ni^{2+}$ other metal ions are of interest for IMAC such as $Cu^{2+}$, $Zn^{2+}$, $Co^{2+}$, $Fe^{3+}$, $Hg^{2+}$.

The use of IMAC for the selection of Histidine-containing peptides from tryptic digests is reviewed in Mirzaei & Regnier (2005) *J. Chrom. B* 817, 23-34. The use of arylboronic acid to couple diagnostic shells to antibodies via the imidazole group is described in WO2006064451, which is based on a copper catalysed reaction described in Collman et al. (2001) *J. Org. Chem.* 66, 1528-1531 (see FIG. 1). Boronic acid is known in the medical field as a reagent which covalently binds to cis-diol groups of sugars above pH 8.0. The use of Boronic acid-modified peptides is described for the inhibition of serine proteases.

SUMMARY OF THE INVENTION

The present invention provides tools and methods for covalently tagging and optionally labelling and selectively isolating Histidine-containing peptides from complex protein mixtures before applying them to subsequent analysis by separation techniques like liquid chromatography followed by spectrometric mass analysis.

One advantage provided by the methods and tools of the present invention is that by the isolation of Histidine-containing peptides after proteolytic cleavage of a protein sample, each protein is represented by a limited number of peptides, leading to a strong reduction in complexity of the sample to be analysed, but without loosing significant information with respect to the protein content of the original protein sample.

Another advantage of the methods and tools of the present invention is that the Histidine-containing peptides of all proteins of the proteome are known (or can be deduced) for those organisms of which the genome has been sequenced (e.g. man, and a number of model organisms such as mouse and rat). The exact molecular weights of these peptides can be predicted, which can be used to support the identification of the peptide generating a signal in MS and optionally the identification of the parent protein.

Particular and preferred aspects of the invention are set out in the accompanying independent and dependent claims. Features from the dependent claims may be combined with features of the independent claims and with features of other dependent claims as appropriate and not merely as explicitly set out in the claims.

The first aspect of the invention relates to a method of covalently attaching an affinity tag to a protein or peptide comprising a Histidine. This method comprises the step of

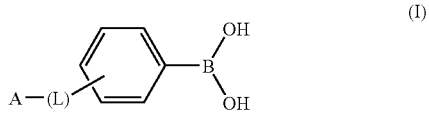

contacting the protein or peptide with a tagging reagent which is a compound with the general structure (I):

wherein A is an affinity tag, B is boron and L is an optional linker, in the presence of a copper catalyst.

According to one embodiment of this method, the compound having general structure (I) is further substituted at the aromatic ring with a halogen, an alkoxy group or an alkyl group.

In specific embodiments of the methods of the invention, the affinity tag A is biotin.

According to a particular embodiment of this method, the tagging reagent is a compound which is a molecule with formula (II):

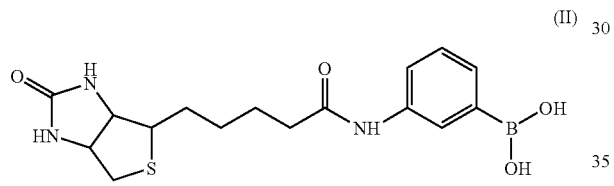

According to another particular embodiment of this method, the tagging reagent is a compound with formula (III):

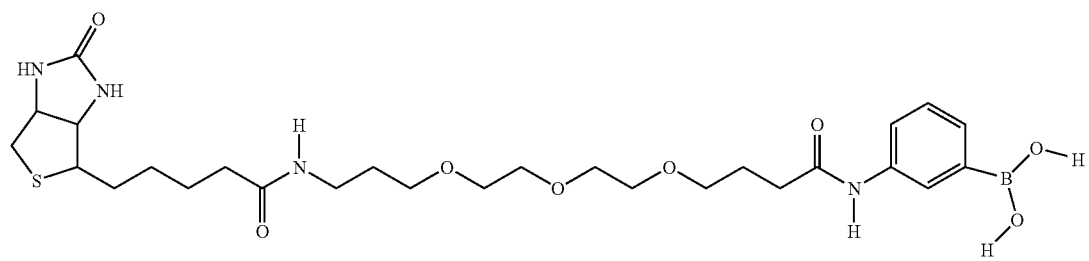

According to a further particular embodiment of the methods of the present invention, the tagging reagent having the general formula (I) more particularly the tagging reagents having a general structural formula corresponding to (II) or (III), further comprise a label. According to a particular embodiment, the label present on the tagging reagents consists of one or more heavy atom isotopes.

A further aspect of the present invention relates to a method for isolating Histidine-comprising peptides from a protein sample or a mixture of pooled protein samples comprising the steps of (a) cleaving the intact proteins in the protein sample(s) with a cleaving agent into peptides, (b) contacting the protein sample(s) with an arylboronic tagging reagent having the general structural formula (I),

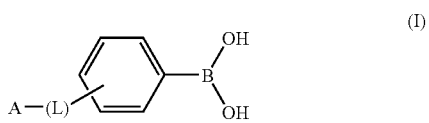

wherein A is an affinity tag, B is boron, and L is an optional linker, in the presence of a copper catalyst, so as to allow reaction of the arylboronic tagging reagent with Histidine where present in the peptides; (c) binding the tagged peptides to an affinity matrix via the affinity tag; and (d) removing the bound tagged peptides from the affinity matrix to obtain the isolated Histidine-comprising peptides.

According to particular embodiments of the methods according to this aspect of the invention, step (b) is performed before/prior to step (a) and the arylboronic tagging reagent is contacted with the uncleaved proteins in the sample(s), resulting in a tagging of Histidine where present in the proteins.

A further aspect of the present invention provides methods for simultaneously analysing the occurrence of one or more proteins comprising Histidine in different samples, which comprises the steps of:

a) optionally cleaving the intact proteins in the sample(s) with a cleaving agent into peptides, b) contacting each of the samples with one of a set of arylboronic acid labelling reagents in the presence of a copper catalyst, whereby the arylboronic acid labelling reagents have the general structural formula (I),

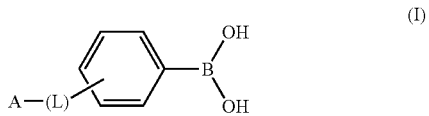

wherein A is an affinity tag, B is boron, and L is an optional linker, and wherein each of the arylborinic reagents of the set further comprise a label which is an isotopic or isobaric label, such that the structure of each of the labelling reagents is essentially the same, c) pooling the different samples to obtain a polypeptide or peptide sample mix, d) selectively isolating the labelled polypeptides or peptides from the polypeptide or peptide sample mix via the affinity tag, and e) analysing the isolated labelled polypeptides or peptides by Mass Spectroscopy so as to determine the occurrence of each of the labelled polypeptides. Whereby the occurrence of the labelled polypeptide is representative of the occurrence of the corresponding protein in the sample.

Yet a further aspect of the present invention provides methods for identifying the presence of a protein in a protein sample comprising the steps of:

a) modifying the amine function of Histidine of the proteins in the protein sample by contacting the proteins with a tagging reagent with the general structure (I):

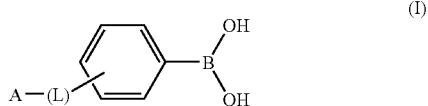

(I)

wherein A is an affinity tag, B is boron and L is an optional linker, in the presence of a copper catalyst, b) cleaving the proteins in the protein sample into peptides with a cleaving agent, c) isolating from these peptides the Histidine-comprising peptides, via the affinity tag, d) purifying the isolated Histidine-comprising peptides by one or more peptide purification steps, so as to obtain purified Histidine-comprising peptides, e) determining or calculating at least one physicochemical property, other than the mass, of the purified Histidine-comprising peptides, f) determining the mass of the isolated and purified Histidine-comprising peptides on MS, and g) comparing, for each isolated and purified Histidine-comprising peptide, the mass and the at least one other physicochemical property to a database comprising the mass and one or more physicochemical properties of all Histidine-comprising peptides generated by the cleaving agent, so as to identify the corresponding parent protein of the purified Histidine-comprising peptide, thereby identifying the presence of the parent protein in the protein sample.

According to one embodiment of this method, step (g) comprises identifying for each of the isolated and purified Histidine-comprising peptides, one or more Histidine-comprising peptides in the database with a mass corresponding to the mass of the isolated and purified Histidine-comprising peptide, and, when more than one peptide are identified for one isolated and purified Histidine-comprising peptide, comparing at least one other physicochemical parameter of the isolated and purified Histidine-comprising peptide with those of the more than one peptides identified in the database.

According to another embodiment of this method, the protein sample is from a species and the database comprises the mass and at least one other physicochemical property of all Histidine-comprising peptides of that species generated by the cleaving agent.

According to one embodiment, the above-described method is used for the simultaneous identification of a protein in two or more samples and the method comprises:

in step (a) performing the modification for each of the samples with one of a set of tagging reagents comprising a differential label component, an additional step of pooling the two or more samples prior to step (d), prior to step (f), the step of identifying the nature of the label so as to identify the sample from which the peptide originates.

According to particular embodiments of the above-described methods, the at least one physicochemical property is determined during the one or more peptide purification steps.

More particularly, the present invention provides embodiments of the methods described above wherein the at least one physicochemical property is selected from the group consisting of pI, retention time during reversed phase chromatography and the ratio of UV absorption at 280 and 214 nm.

Yet a further aspect of the present invention provides tagging reagents for tagging Histidine in a protein or peptide, the compounds having the general structure (I):

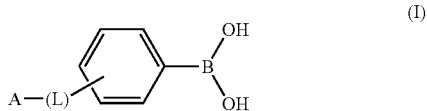

(I)

wherein A is an affinity tag selected from the group consisting of biotin or a biotin-derived molecule, maltose, a lectin, a hapten binding to hapten-specific antibodies, and glutathione, B is boron and L is an optional linker.

In particular embodiments of the tagging reagents, the aromatic ring of structure (I) is further substituted with a halogen, an alkoxy group or an alkyl group.

In another embodiment, the affinity tag A on the compound is biotin.

In a particular embodiment, the tagging reagents of the present invention have the structure of formula (II):

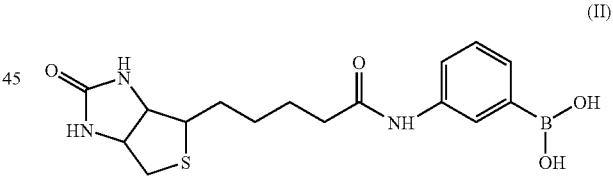

(II)

In another particular embodiment, the tagging reagents of the present invention have the structure of formula (III):

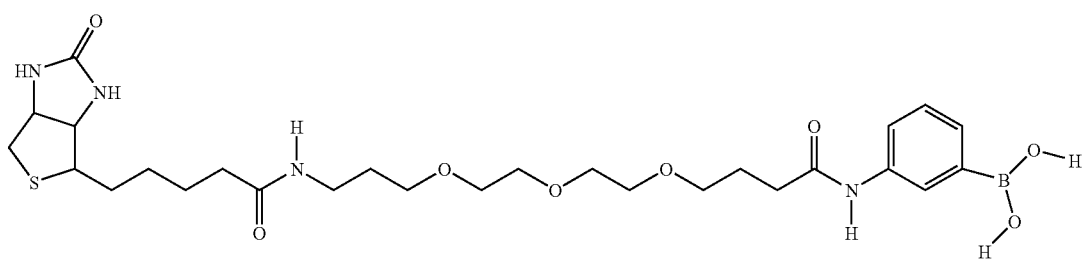

(III)

Particular embodiments of the tagging reagents of the present invention further comprise a labelling component, more particularly, a labelling component consisting of one or more heavy isotopes. More particularly, the tagging reagents have the general structure of formula (I), whereby one or more carbon atoms and/or one more hydrogen atoms in the linker (L) between the Affinity tag and the arylboronic group are replaced by respectively $^{13}C$ or deuterium. In a further particular embodiment, the tagging reagent of the present invention has the general structure of formula (III), whereby one or more carbon atoms and/or one more hydrogen atoms in the linker between the biotin group and the arylboronic group are replaced by respectively $^{13}C$ or deuterium.

Yet a further aspect of the present invention relates to a set of labelling reagents for mass spectrometry analysis of polypeptides, wherein all labelling reagents in the set have an identical chemical structure (I) as described, and wherein each labelling reagent in the set has a unique isotopic label component.

In one embodiment of the sets of labelling reagents of the invention, the individual labelling reagents of the set have a structure according to formula (III): wherein one or more carbon atoms and/or one or more hydrogen atoms in the linker between the biotin group and the arylboronic group are replaced by respectively $^{13}C$ or deuterium.

the present invention, a protein cleavage unit (105), an affinity separation unit (106) a separation unit (107), a mass spectrometer unit (109) and a data analysis unit (110) connected with annotated database (112) of in silico cleaved Histidine comprising peptides.

In one embodiment, the device further comprises a sample preparation unit (102) and/or an analysis unit (108) for determining one or more physicochemical properties of the peptides purified in the separation unit (107).

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference Figures quoted below refer to the attached drawings.

BRIEF DESCRIPTION OF THE DRAWINGS

FIG. 2 shows in accordance with a particular embodiment of the present invention the copper catalysed reaction of an

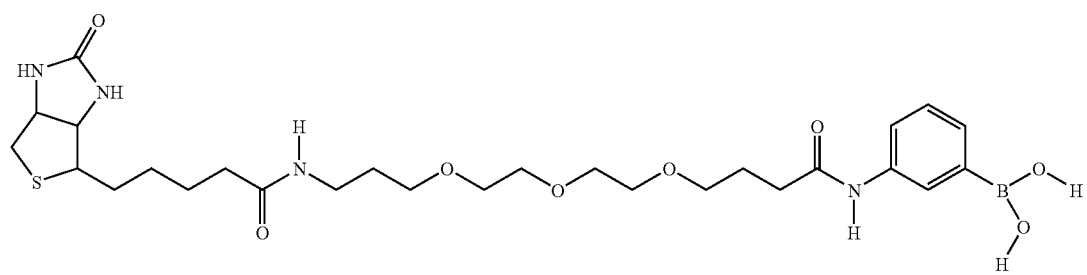

(III)

A further aspect of the present invention relates to the use of a tagging reagent and combined tagging and labelling reagents described above for the tagging and (differential) labelling of proteins.

A further aspect of the present invention provides a database of Histidine-comprising peptides of proteins of an organism cleaved in silico by a cleaving agent wherein each peptide is characterised by a protein identifier, its amino acid composition and its mass, wherein the mass is the mass of the unmodified peptide or the mass of the peptide after modification or labelling.

In one embodiment of the databases provided in the present invention, peptides in the database with a differing sequence and a same mass are further characterised by at least one physicochemical parameter of the peptide other than its mass.

In another embodiment, the databases of the present invention, are databases of Histidine-comprising peptides of proteins of an organism cleaved in silico by a cleaving agent which is trypsin.

Yet another aspect of the present invention relates to the use of a database as described above for the identification of proteins.

Yet another aspect of the present invention relates to a device (100) for multiplex labelling and analysis of protein samples comprising at least one source of samples (101), a tagging and labelling unit (103) and corresponding tagging/labelling reagent sources (104) for the arylboronic reagents of arylboronic tagging reagent with Histidine present in a polypeptide as exemplified in example 2.

Figure 3:
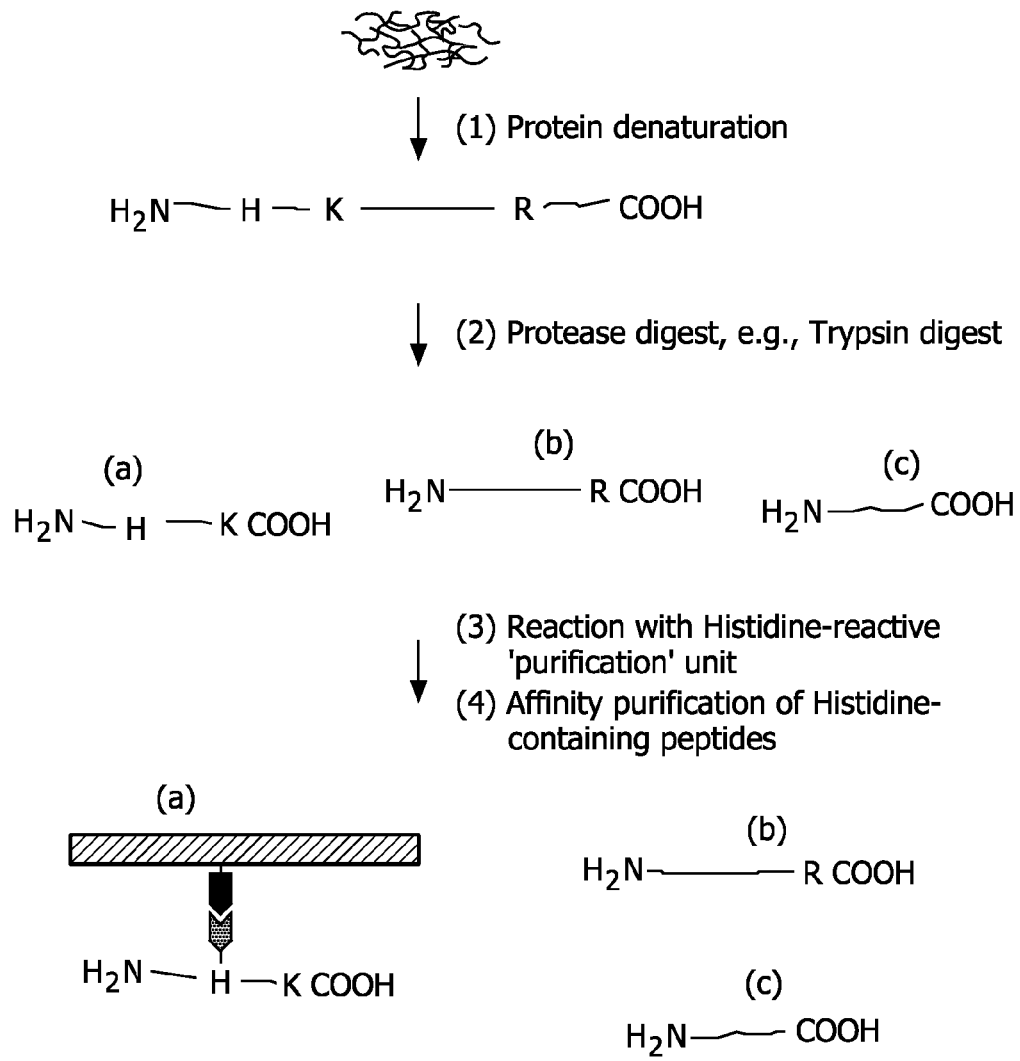

FIG. 3 demonstrates in accordance with a particular embodiment of the present invention a method for the selective isolation of Histidine-comprising peptides from a protein solution. (1): protein denaturation; (2): proteolytic cleavage into N-terminal (a), internal (b) and C-terminal (c) peptides; (3): reaction with a Histidine-reactive tagging reagent; (4) coupling of tagged peptides via the affinity tag (grey arrow) to an solid support with a capture reagent (black arrow).

Figure 4:
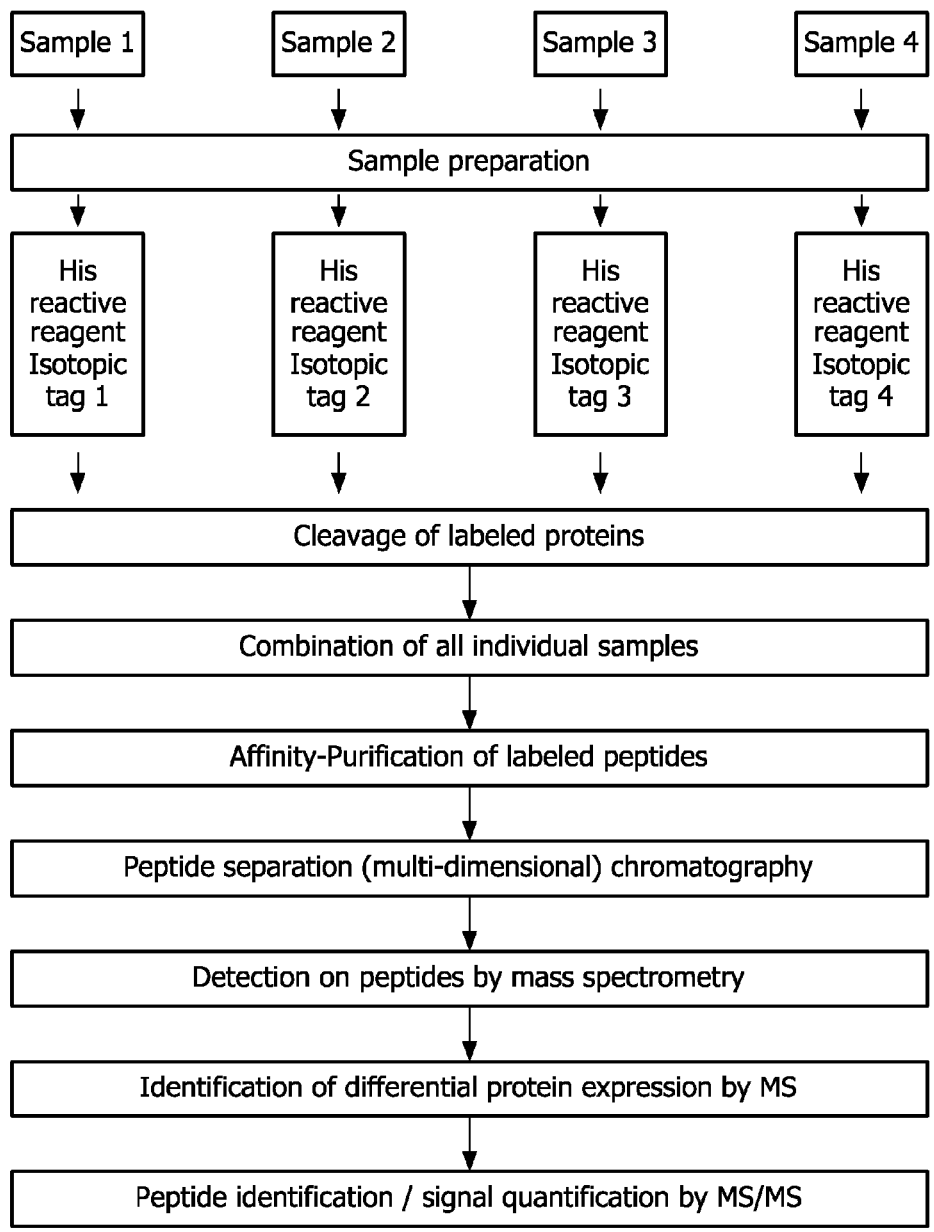

FIG. 4 demonstrates the simultaneous analysis of multiple samples using Histidine reactive labelling reagents comprising an isotopic label component in accordance with particular embodiments of the present invention.

Figure 5:
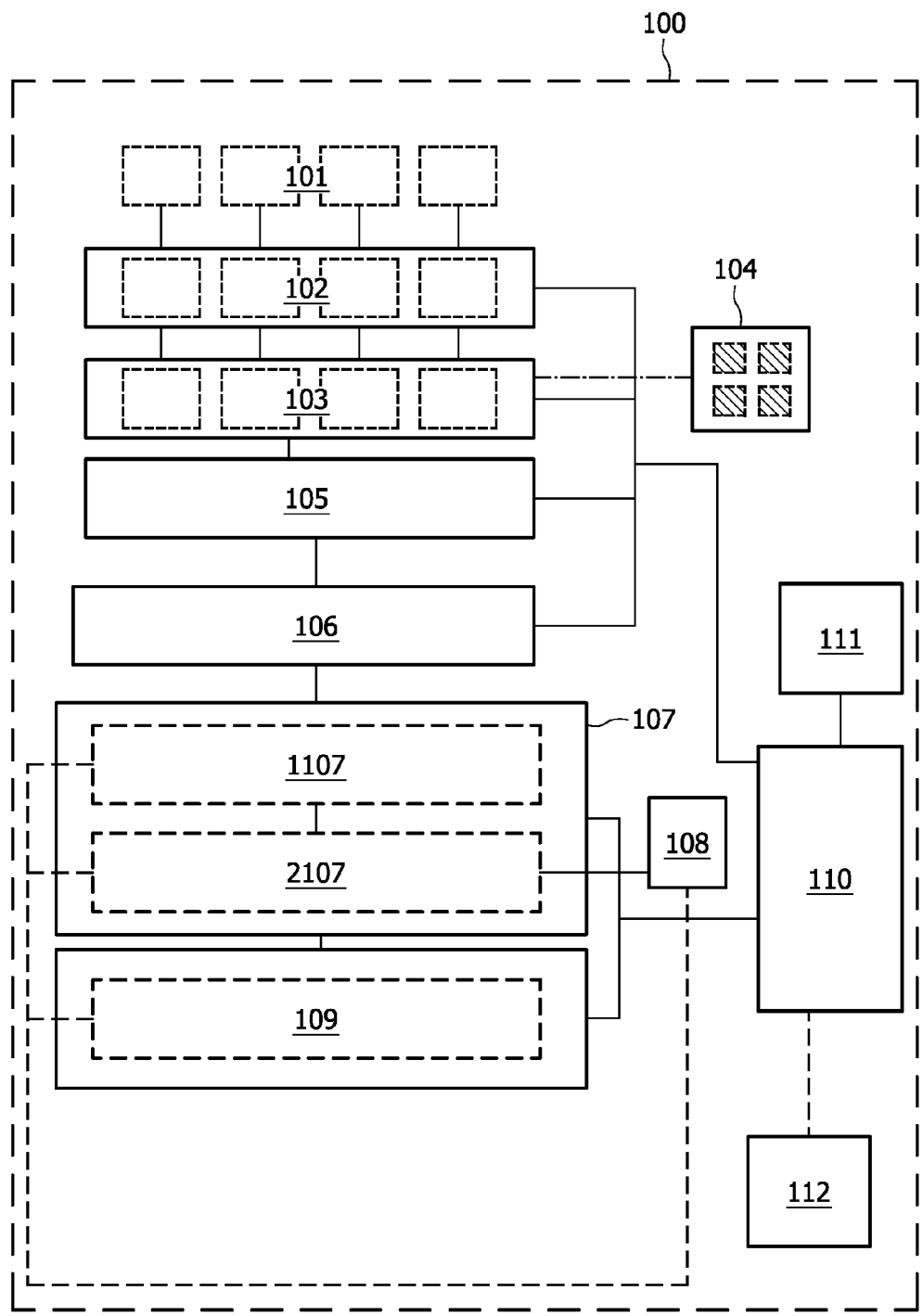

FIG. 5 shows in accordance with a particular embodiment of the present invention a device (100) for multiplex analysis of 4 protein samples, comprising at least four sample sources (101), a sample preparation unit (102), a labelling unit (103) with labelling reagent sources (104), a protein cleavage unit (105) an affinity-purification unit (106) (e.g. avidin affinity chromatography system), a separation unit (107) comprising two consecutively coupled separation systems (1107) and (2107), a mass spectrometer unit (109) and a control and analysis circuitry and data analysis unit (111) coupled to a read out system (112). Unit (108) is an analysis unit for determining physicochemical properties of peptides purified in unit (107) and unit (110) comprises an annotated database of Histidine-comprising peptides. (dotted lines indicate the acquisition of experimental and in silico data).

Figure 6:
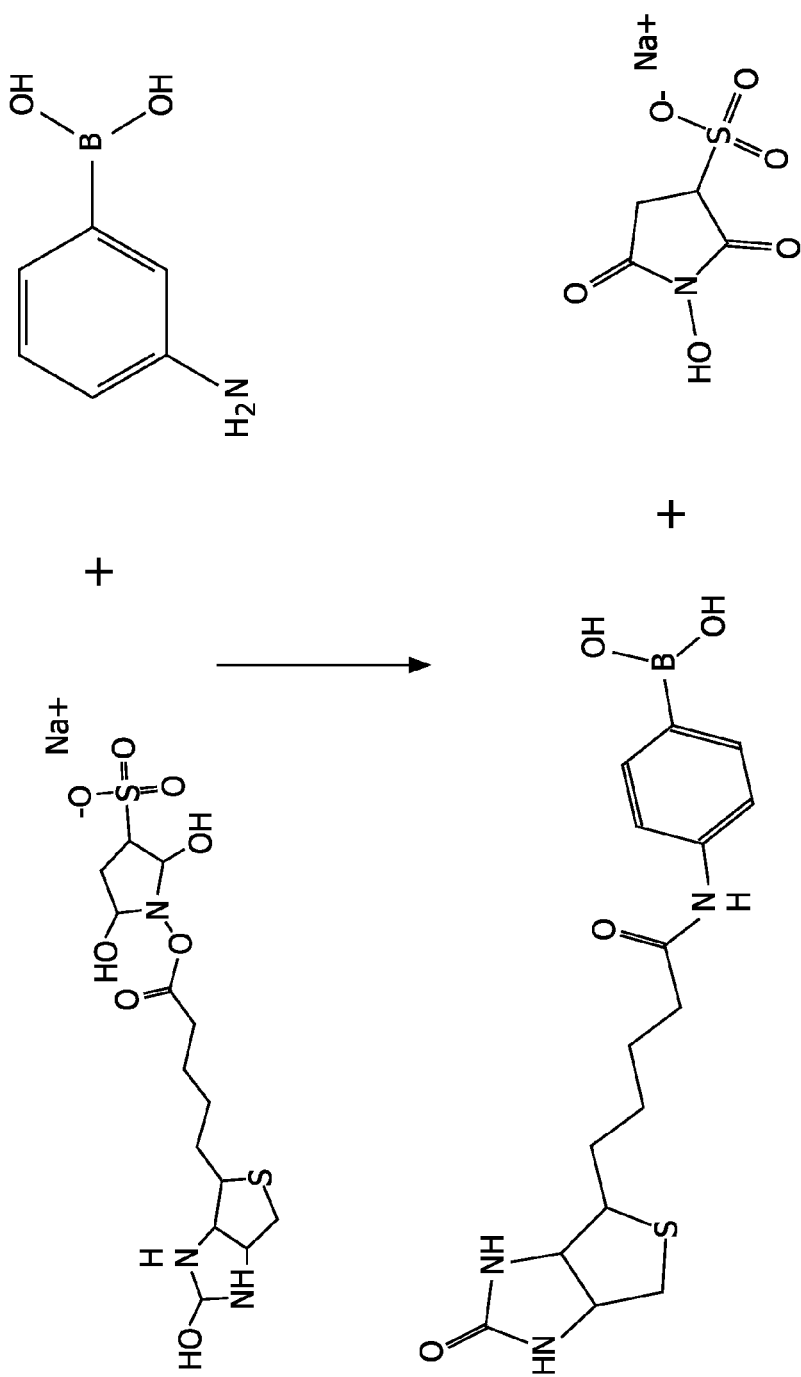

FIG. 6 shows the synthesis of the tagging reagents in accordance with a particular embodiment of the present invention based on the reaction of NHS functionalised biotin with m-aminophenylboronic acid as exemplified in Example 1.

Figure 7:
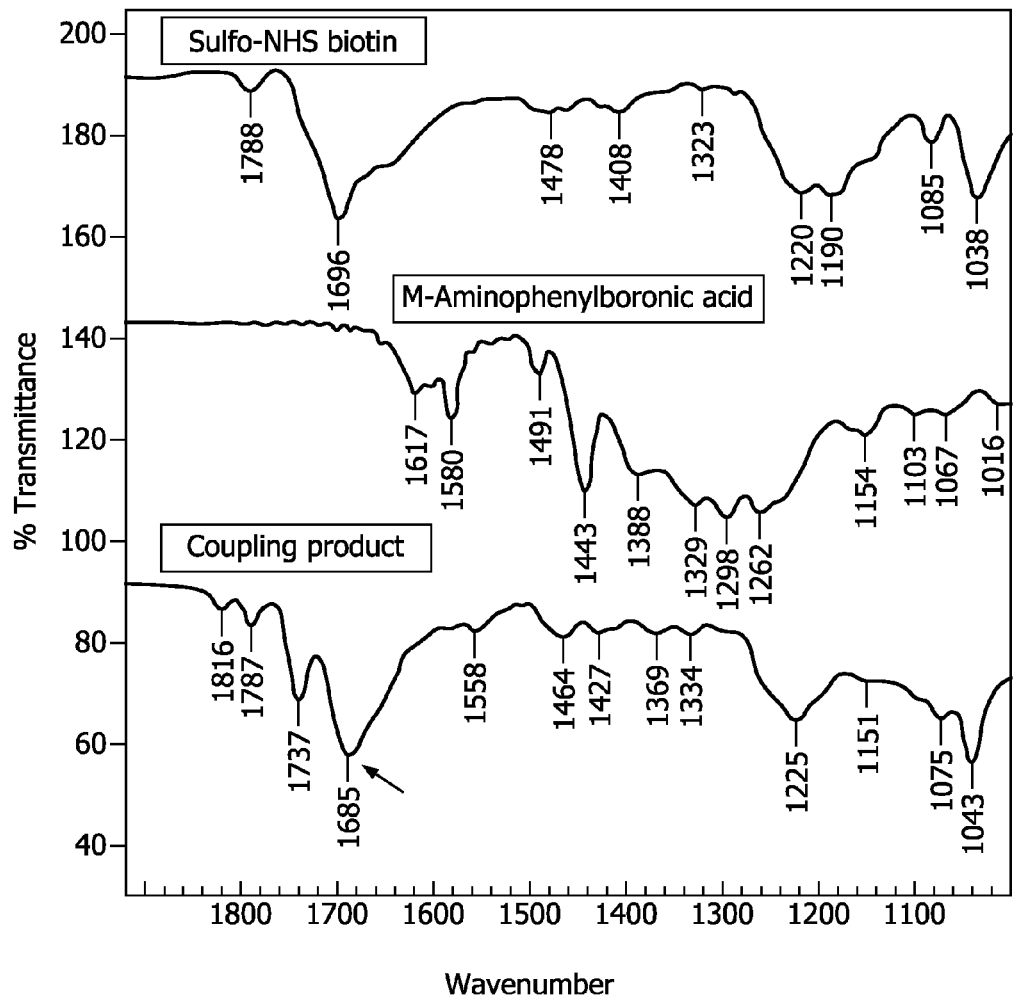

FIG. 7 shows in accordance with a particular embodiment of the present invention the IR spectra of reactants and the reaction mixture in the synthesis described in Example 1.

Figure 8A:
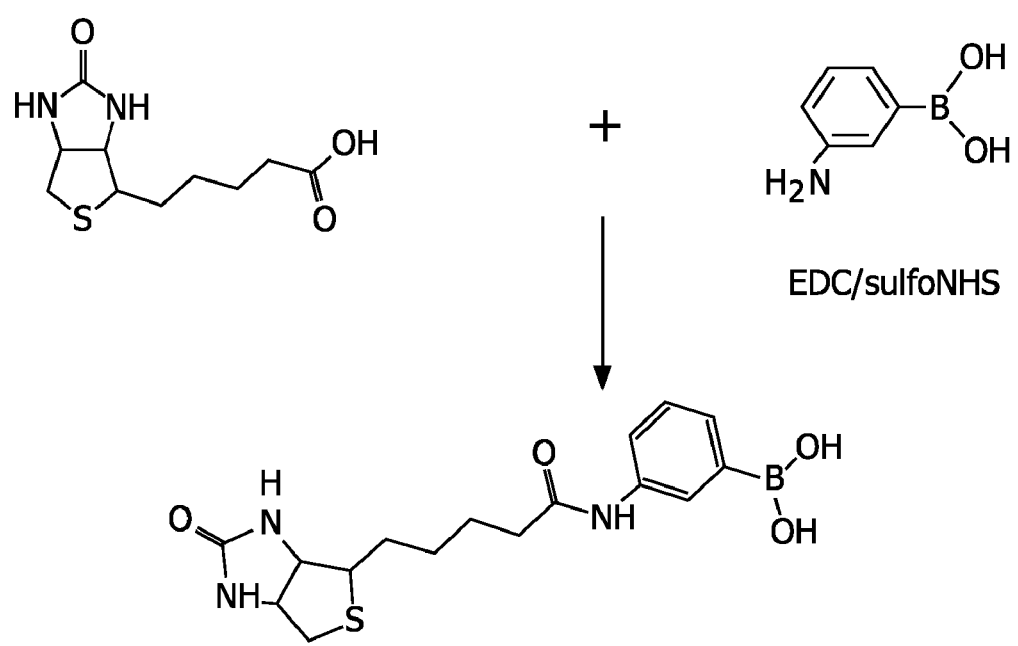
Figure 8B:
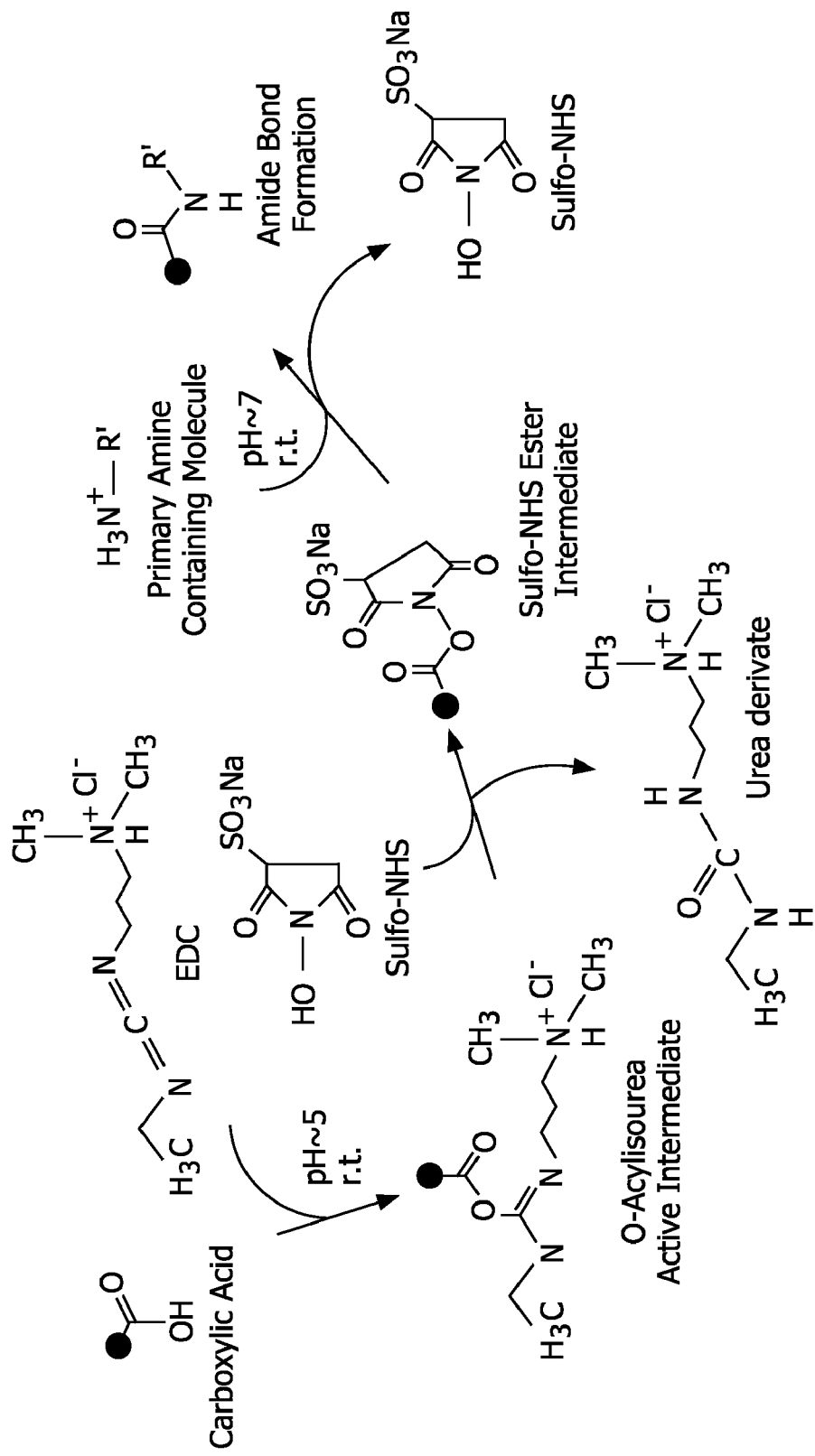

FIG. 8 shows in panel A the EDC mediated coupling of biotin to m-aminophenylboronic acid in accordance with a particular embodiment of the present invention and in panel B the detailed reaction scheme of the generalised reaction as shown in panel A wherein the biotin group is replaced by a black circles.

Figure 9:
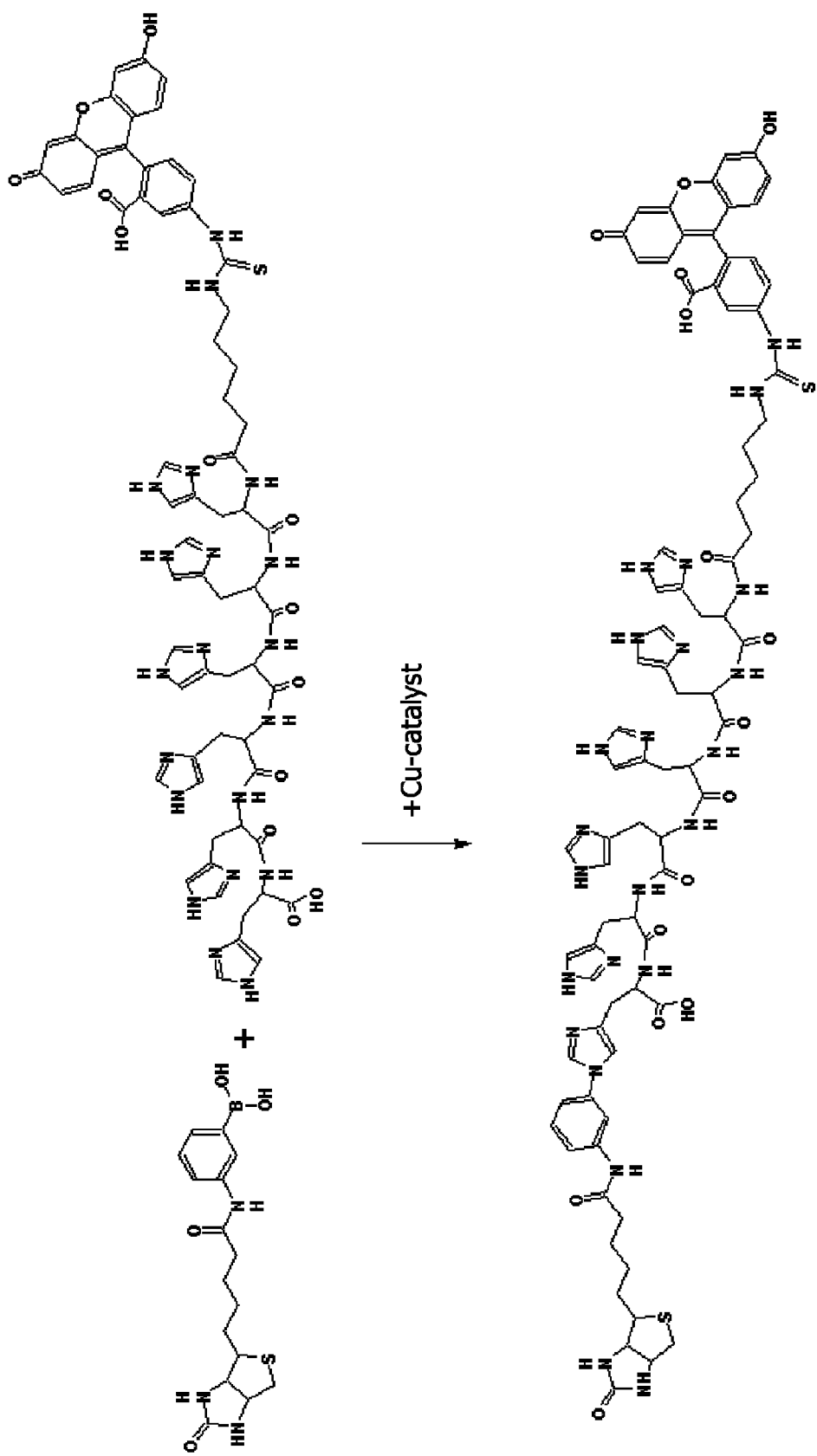

FIG. 9 shows in accordance with a particular embodiment of the present invention the copper catalysed reaction of the tagging reagent with a Histidine comprising peptide as exemplified in example 2.

DETAILED DESCRIPTION OF THE EMBODIMENTS

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The following terms or definitions are provided solely to aid in the understanding of the invention. These definitions should not be construed to have a scope less than understood by a person of ordinary skill in the art.

The term "polypeptide" or "protein", as used herein, refers to a plurality of natural or modified amino acids connected via a peptide bond. The length of a polypeptide can vary from 2 to several thousand amino acids (the term thus also includes what is generally referred to as oligopeptides). Included within this scope are polypeptides comprising one or more amino acids which are modified by in vivo posttranslational modifications such as glycosylation, phosphorylation, etc. and/or comprising one or more amino acids which have been modified in vitro with protein modifying agents (e.g. alkylating agents).

The term "polypeptide fragment" or "peptide" as used herein is used to refer to the amino acid sequence obtained after cleavage of a protein or polypeptide. A polypeptide fragment or peptide is not limited in size or nature.

The terms "internal", "aminoterminal" and "carboxyterminal" when referring to a peptide are used herein to refer to the corresponding location of a peptide in a protein or polypeptide. For example, in a tryptic cleavage of protein $NH_2$—$X_1$—$K$—$X_2$—$R$—$X_3$—$K$—$X_4$—COOH (wherein $X_1$, $X_2$, $X_3$ and $X_4$ are peptide sequences of indifferent length without Lysine (K) or Arginine (R)), the aminoterminal peptide is $NH_2$—$X_1$—K—COOH, the internal peptides are $NH_2$—$X_2$—R—COOH and $NH_2$—$X_3$—K—COOH and the carboxyterminal peptide is $NH_2$—$X_4$—COOH.

The term "protein cleavage" as used herein relates to the hydrolysis of a peptide bond between two amino acids in a polypeptide. This includes both chemical or enzymatic hydrolysis. Accordingly the term "cleaving agent" as used herein refers to a compound capable of hydrolysing a peptide bond between two amino acids in a polypeptide or peptide.

The term "parent protein" refers to the uncleaved protein from which a cleaved peptide is derived.

The term "fragmentation" as used herein refers to the breaking of one or more chemical bonds and subsequent release of one or more parts of a molecule as obtained e.g. by collision-induced dissociation (CID) in Tandem Mass spectrometry (MS) or MS/MS analysis. In certain embodiments the bond is a peptide bond, but it is not limited thereto.

The term "protein/peptide reactive group (PRG)" as used herein refers to a chemical function on a compound (e.g. a labelling reagent) that is capable of reacting with a functional group on an amino acid of a protein or peptide resulting in the binding (non-covalent or covalent) of such compound to the amino acid. The present invention provides aryl boronic acid molecules according to the structure described below as protein/peptide reactive groups reacting with the functional group of amino acid Histidine.

The term "tag" or "affinity tag" as used herein refers to a chemical structure which can be covalently linked to a peptide or polypeptide, and which, based on its specific interaction with another chemical structure, can be used to isolate the peptide or polypeptide to which it is bound from a mixture. Accordingly, the term "tagging reagent" as used herein comprises the unbound tag, prior to reaction with a protein or peptide, and comprises a protein/peptide reactive group for covalent binding of the tag to a protein or peptide. In the tagging reagents of the present invention, the protein/peptide reactive group (PRG) is an arylboronic acid which reacts with Histidine.

The term "label" as used herein refers to a chemical structure which is or can be covalently linked to a peptide or polypeptide and which, based on its particular properties is detectable on a mass spectrometer, or by optical methods. Generally the term "label" will be used to refer to the molecule as present on the polypeptide or peptide, and the term "labelling reagent" is used to refer to the combination of the label component and the protein/peptide reactive group. The label component (i.e. part of the labelling reagent generating the label) can be incorporated into the protein/peptide reactive group of the labelling reagent or can be a separate chemical structure within, or bound onto, the protein reactive group. Where a tagging reagent according to the present invention comprises a label component this reagent can be used as a labelling reagent and will be referred to as such.

The term "mass" in the present invention refers to the mass-to-charge ratio (m/z). The abbreviation m/z is used to denote the dimensionless quantity formed by dividing the mass number of an ion by its charge number. The "monoisotopic mass" refers to the mass of the ion containing only the most abundant isotopes. "Average mass" refers to the mass of a particle or molecule of given empirical formula calculated using atomic weights for each element.

The term "isotopic labels" and "isotopic labelling reagents" as used herein refers to a set of labels and labelling reagents having the same chemical formula but differing from each other in the number and/or type of isotopes present of one or more atoms, resulting in a difference in mass on MS. Thus, identical peptides labelled with different isotopic labels can be differentiated as such on MS based on difference in mass. While isobaric labels (see below) in principle constitute a specific type of isotopic labels, in the context of the present invention, the term isotopic label will be used to refer to labels which are not isobaric, but can as such be differentiated based on their molecular weight without fragmentation.

The term "isobaric labels" and "isobaric labelling reagents" as used herein refers to a set of labels having the same structure, and the same mass, which upon fragmentation release a particular fragment with the same structure for all isobaric labels of that set, which differs in mass between the individual isobaric labels in that set, due to a differential distribution of isotopes within the isobaric labels. Isobaric labels typically comprise a reporter group (RG), which is a relatively small fragment and a balance group (BG). The "combined mass" of a set of isobaric labels refers to the total mass of the reporter group and the balance group for that set of isobaric labels.

The term "functional group" as used herein refers to a chemical function on an amino acid, which can be used for binding (generally, covalent binding) to a chemical compound. Functional groups can be present on the side chain of an amino acid or on the aminoterminus or carboxyterminus of a polypeptide or peptide. The term encompasses both functional groups which are naturally present on a peptide or polypeptide and those introduced via e.g. a chemical reaction using protein-modifying agents.

One aspect of the invention relates to tagging reagents which are compounds comprising a protein reactive group reacting with the imidazole functional group of Histidine and comprising an affinity tag. More particularly, the PRG which reacts with Histidine is a substituted or unsubstituted aryl boronic acid.

The reagents of the present invention are generally referred to as substituted arylboronic acids, having a general structure (I):

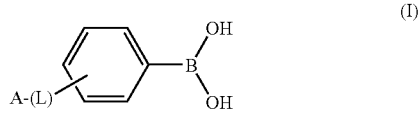

wherein A is an affinity tag, B is boron, and L is an optional linker.

The A-(L)- group on the benzene can be in ortho, meta or para position with B(OH)$_2$.

In particular embodiments of the reagents of the present invention, the remaining positions of the benzene group, are substituted with one or more substituents independently selected from the group consisting of an alkyl (e.g. methyl, ethyl, propyl), a halogen (e.g. F), an alkoxy (e.g. methoxy), or a functional group such as a carboxyl group, an amino group or a thiol.

The preparation of the reagents of the invention is performed in accordance with commonly known methods in organic chemistry for the preparation of protein labelling reagents. Typically this is ensured by reacting arylboronic acids (or alkylarylboronic acids) comprising an additional functional group (e.g. amino group) with an affinity tag or a linker carrying a functional group capable of reacting with the functional group on the arylboronic acid so as to result in a covalent bond. The preparation of a number of compounds is illustrated in the examples section. The tagging reagents of the present invention ensure the binding of an affinity tag (A) to a protein or peptide which tag can be used for selective isolation of the proteins or peptides to which the tag is bound.

The nature of the affinity tag in the compounds and methods of the present invention is not critical. Typical examples of well-established affinity tags include d-biotin (or biotin-derived molecules), maltose and other sugar/sugar binding, hapten binding to hapten-specific antibodies, and glutathione. Further embodiments of affinity tags useful in the context of the present invention are detailed below.

Affinity tags can be bulky and may require the presence of a linker L between the PRG and the affinity tag. The linker L can be a molecular structure serving only this purpose (i.e. distancing the affinity tag from the protein reactive group to avoid interference) or can at the same time comprise all or part of the label component (as detailed below). Additionally or alternatively the linker may provide a cleavable bond between the affinity tag and the rest of the compound (also detailed below).

A particular embodiment of the present invention provides the tagging reagents as described above, which, in addition comprise a label component. More specifically a set of two or more tagging reagents is provided each tagging reagent within the set comprising one of a set of label components for differential labelling of proteins or peptides in mass spectrometry. According to this embodiment, the tagging reagents of the present invention are referred to as labelling reagents.

According to one embodiment, the labelling reagents of the present invention comprise as a label component, a group which is detectable by optical methods e.g. adsorbs visible or UV light, or is fluorescent or phosphorescent.

According to particular embodiment however, the labelling reagents of the present invention comprise a label component, which is an isotopic label component (i.e. a label component belonging to a set of isotopic label components). Accordingly, the use of such isotopic labelling reagents allows the identification of differentially labelled peptides within a pooled peptide mixture.

According to one embodiment, the isotopic label components in the isotopic labelling reagents of the present invention comprise an identical molecular structure wherein, in each label component, one or more of the atoms are substituted with a stable isotope, so as to generate two or more compounds with the same chemical formula, but which are isotopically distinguishable based on their difference in mass. For example, any one or more of the hydrogen, nitrogen, oxygen or sulphur atoms in the isotopic label component can be replaced with their isotopically stable isotopes $^2$H, $^{13}$C, $^{15}$N, $^{17}$O, $^{18}$O or $^{34}$S, respectively. For example, hydrogen is substituted with deuterium or carbon $^{12}$C is substituted with $^{13}$C. Using one more of the above isotopes, 2, 3, 4, 5, 6, 7, 8, or an even higher number of isotopic label components can be generated, each having the same structure but with a different Mr. As indicated above, the difference in Mr of these label components, upon binding of each of the labelling reagents on identical polypeptides in a different sample, is reflected in the resulting Mr of the polypeptide or peptide generated therefrom.

Examples of groups which can function as isotopic label components by differential introduction of one or more isotopes include but are not limited to ethers, polyethers, ether diamines, polyether diamines, diamines, amides, polyamides, polythioethers, disulfides, silyl ethers, alkyl or alkenyl chains (straight chain, branched or with portions which are cyclic), aryl, diaryl or alkyl-aryl groups. In particular embodiments, aryl groups present in the isotopic component of the labelling reagents of the present invention contain one or more heteroatoms (e.g., N, O or S atoms).

According to a particular embodiment, the isotopic label component of the labelling reagent is such that it does not undergo peptide-like fragmentation during $(MS)^n$ analysis. To promote ionization, the isotopic label component, and more particularly the isotopic group therein, may contain groups or moieties such as acidic or basic groups, e.g., COOH, $SO_3H$, primary, secondary or tertiary amino groups, nitrogen-heterocycles, ethers, or combinations of these groups. In particular embodiments, the isotopic label component contains groups having a permanent charge, e.g., phosphonium groups, quaternary ammonium groups, sulfonium groups, chelated metal ions, tetralky or tetraryl borate or stable carbanions.

The isotopic label component of the labelling reagents of the present invention can be a separate part of the molecule or can be incorporated in or combined with the protein reactive group. According to the latter embodiment, the isotopes of the isotopic label component can be incorporated in the aromatic group of the arylboronic acid, in substituents on this aromatic ring, or in the linker (L), when present, which connects the arylboronic acid with the affinity tag The preparation of isotopic labelling reagents according to this embodiment of the invention is similar to the preparation of isotopic labelling reagents disclosed in the examples of U.S. Pat. No. 6,852,544, wherein the protein reactive group is an arylboronic acid.

According to another embodiment, the labelling reagents of the present invention comprise, as label components, an isobaric label component. Similar to the isotopic label component comprising reagents, the use of isobaric labelling reagents allows the identification of differentially labelled peptides within a pooled peptide mixture.

Isobaric labelling components for use in the context of the present invention have been described in the art. As detailed above, isobaric label components comprise a reporter group (RG), which is a relatively small fragment and a balance group (BG), whereby the combined mass of the reporter group and the balance group is identical for all isobaric label components within a set, while the mass of the RG is different for each isobaric label component within the set and is used for the differential identification of identical peptides.

In those embodiments wherein an isobaric label is present, the affinity tag is typically placed at a position where it does not interfere with the release of the reporter group after Collision-Induced Dissociation (CID).

The isobaric labelling component of the labelling reagents of the present invention can be a separate structure. Alternatively, the reporter and balance groups are typically parts of the linker or substituents of the linker. In particular embodiments, the aromatic ring and substituents thereon are used to incorporate isotopes and to act as a balance group. In very particular embodiments, the structure connecting the affinity tag with the Histidine-reactive group, which can be considered as a linker, acts as an isobaric labelling component whereby the main structure of the linker is the balance group and the reporter group resides on a side chain of the linker. In an other very particular embodiment, both balance group and reporter group are a part of the linker by the specific distribution of isotopes in dedicated regions of the linker and providing bonds adjacent to the reporter group which are susceptible to cleavage by CID, for release of such reporter group.

The preparation of isobaric labelling reagents according to this aspect of the present invention in one embodiment corresponds to the preparation of isobaric labelling reagents disclosed in the examples of WO2004070352, wherein the protein reactive group is an (alkyl)arylboronic acid.

As indicated above, the presence of an affinity tag in the tagging and labelling reagents of the present invention, allow the selective binding of tagged and optionally labelled peptides or polypeptides, either covalently or non-covalently and with high affinity to a capture reagent (CR). Typically the binding of the affinity tag to the capture reagent is strong such that it is resistant to extensive and/or multiple washing with any or a combination of a variety of solutions which ensure the removal of peptides or polypeptides non-specifically bound to the capture reagent. Typically the affinity tag does not undergo peptide-like fragmentation during MS analysis.

As indicated above, and more particularly for use in the methods of the present invention, the nature of the affinity tags is not critical, as long as it allows the selective binding to a capture reagent (CR) and optionally removal therefrom, without affecting the peptide or polypeptide bound to the affinity tag.

Accordingly, non-limiting examples of Affinity tags (A) and capture reagent (CR) pairs include:

d-biotin or structurally modified biotin-based reagents, including d-iminobiotin, which bind to avidin/streptavidin (for example as strepavidin-Agarose, oligomeric-avidin-Agarose, or monomeric-avidin-Agarose), maltose which binds to Maltose Binding Protein; or other sugar/Sugar Binding Protein pairs, or more generally to any ligand/Ligand Binding Protein pair which obeys to the above mentioned criteria of affinity tags, a hapten, such as dinitrophenyl group, which binds to the corresponding anti-hapten antibody such as anti-dinitrophenyl-IgG, glutathione which binds to glutathione-5-transferase.

In particular embodiments of the present invention, an affinity purification of labelled peptides or polypeptides is performed prior to analysis by MS. Accordingly, as the bound peptides or polypeptides are required for further analysis, removal from the capture reagent or dissociation of the affinity tag from the peptide is required. This can be ensured in different ways.

In particular embodiments, the affinity tag is connected to the labelling reagent by a cleavable bond (such as, but not limited to an acid labile, thiol labile, base labile, periodate labile, or hydroxylamine labile bond).

In further particular embodiments, the bond between affinity tag and labelling reagent can also be cleavable by chemical, thermal or photochemical reaction. A suitable photocleavable group is 1-(2-nitrophenyl)-ethyl. Thermally labile bonds are for example, double-stranded nucleic acids, double strands of a nucleic acid with peptide nucleic acid, or double stranded peptide nucleic acid strands which will dissociate upon heating. Cleavable groups also include those having disulfide bonds, acid or base labile groups, periodate labile, or hydroxylamine labile groups including among others, diarylmethyl or trimethylarylmethyl groups, silyl ethers, carbamates, oxyesters, thiesters, thionoesters, and alpha-fluorinated amides and esters. Enzymatically cleavable groups are for example, protease-sensitive amides or esters, beta-lactamase-sensitive beta-lactam analogues and bonds that are nuclease-cleavable, or glycosidase-cleavable.

According to this embodiment, the affinity tag can be removed by treatment of the labelled protein or peptide with a suitable reagent. Removal of the affinity tag may also be desirable for other reasons, e.g. to avoid interference in analysis of the peptide, e.g. in MS. Typically, the affinity tag is cleaved off after the affinity isolation of labelled peptides or polypeptides.

Alternatively, the affinity tag can be present in the tagging and labelling reagents of the present invention linked to the protein/peptide reactive group with a non-cleavable bond. In order to ensure that the affinity purified peptides can be recuperated, if the affinity tag is not removable, an affinity tag is used which can in some way be dissociated from the capture reagent (CR). In particular embodiments, biotin and biotin-based affinity tags are used. Of particular interest are structurally modified biotins, such as d-iminobiotin, which will elute from avidin or streptavidin columns under solvent conditions compatible with ESI-MS analysis, such as dilute acids containing 10-20% organic solvent. It has been established that d-iminobiotin tagged compounds will elute in solvents below pH 4.

Additionally or alternatively, displacement ligands (DL) are used to displace the affinity tag (A) (and the peptide or protein bound thereto) from the capture reagent (CR). When eluting with a DL at least a fraction of this DL will be present in the eluent comprising the peptide(s) of interest. In particular embodiments the methods of the invention can comprise the use of a DL which is a molecule which does not undergo peptide-like fragmentation during MS analysis, and of which the presence in a sample does not significantly suppress the ionisation of the tagged peptide, substrate or reaction product conjugates. Particularly, the displacement ligand can be chosen such that it itself is minimally ionised during mass spectrometric analysis and that the formation of ions composed of DL clusters is minimal.

components or for the reporter group of an isobaric label component. As indicated above, In very particular embodiments, the linker acts as a balance group and the reporter groups reside on a side chain of the linker. In another very particular embodiment, both balance group and reporter group are a part of the linker by the specific distribution of isotopes in dedicated regions of the linker and providing bonds adjacent to the reporter group which are susceptible to cleavage by CID, for release of such reporter group.

In particular embodiments of the present invention, the affinity tag present in the tagging or labelling reagent is biotin. In further particular embodiments, the arylboronic acid is phenylboronic acid. In a very particular embodiment the compound of the present invention is a molecule with formula (II):

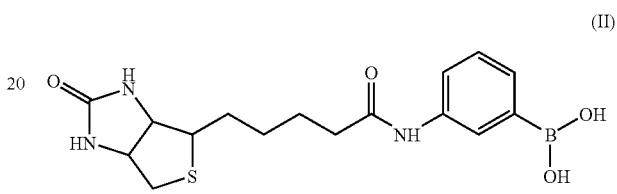

(II)

wherein the general structure in addition comprises, as a label component one or more 'heavy' isotopes.

In a further particular embodiment the labelling reagent of the present invention is a molecule with formula (III).

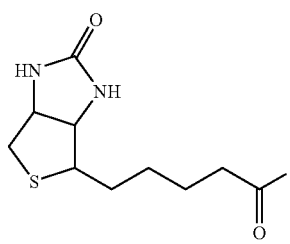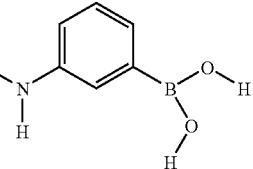

(III)

The nature of a suitable displacement ligand (DL), depends upon the nature of the A and CR that are employed. In general, the DL is selected to displace A from CR in a reasonable time scale, at most within a week of its addition, but more preferably within a few minutes or up to an hour. The affinity of DL for CR should be comparable or stronger than the affinity of the tagged compounds containing A for CR. Furthermore, the DL should be soluble in the solvent used during the elution of tagged compounds containing the affinity tag A, from CR. In particular embodiments the DL corresponds to a free affinity tag A or a derivative or structural modification of A. Examples of displacement ligands thus include, d-biotin or d-biotin derivatives.

As referred to above, in some embodiments of the present invention, the tagging or labelling reagents comprise a linker between the affinity tag and the Histidine-reactive group (arylboronic acid). This linker can be the remainder of the reaction between the (alkyl)aryl boronic acid and the affinity tag. The linker can also be used to physically separate a (bulky) affinity tag from the protein reactive group, so as to prevent interference of the affinity tag in the binding of the reagent to the peptide. As indicated above, in the labelling reagents of the present invention, the linker can optionally incorporate isotopes or function as a scaffold for optical label wherein optionally one or more carbon atoms and/or one more hydrogen atoms in the linker between the biotin group and the arylboronic group are replaced by respectively $^{13}C$ or deuterium.

The tagging and labelling reagents described above can be used for reducing the complexity of protein samples by allowing the selective isolation of Histidine-comprising peptides.

In order for a tagging and/or labelling reagent to ensure the selective isolation of a representative number of peptides, the reagent ideally targets almost every protein in a sample to obtain a maximal coverage of the proteome in a sample. At the same time, when considering each individual protein, the number of functional groups in the protein reacting with the reagent is ideally low, so as to reduce the complexity of the analysis (number of peptides to be analysed from this protein in a sample is only one or a limited number).

In the tools and methods of the present invention, Histidine is used as the functional group for tagging and/or labelling. Histidine labelling provides an acceptable compromise between maximal coverage (labelling every protein in a sample) and minimal complexity (labelling every protein in a sample only once or a limited number of times). Histidine occurs with a frequency of 2-3% (one in each 30-50 amino acids) in a polypeptide sequence. Furthermore, labelling with Histidine does not modify other parts of a protein as is the case with the labelling amine groups which occur on both Lysine and the aminoterminus or as is the case with labelling carboxyl groups which occur on both Aspartic acid, Glutamic acid and the carboxyterminus.

Figure 2:
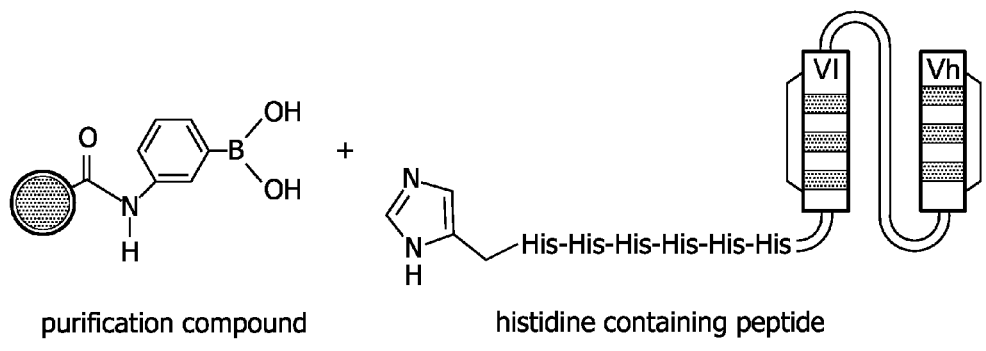
Figure 2:
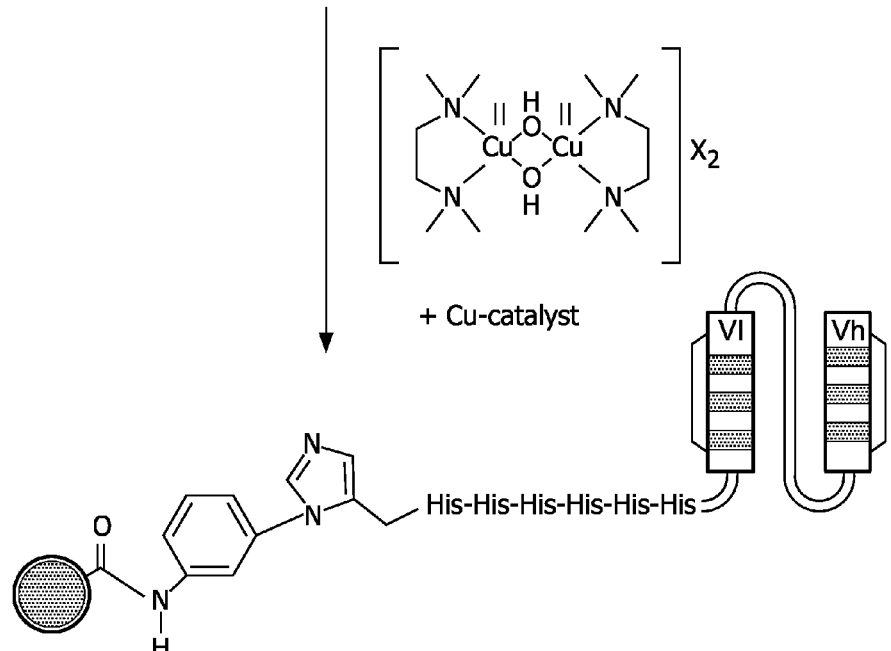

Accordingly the use of the reagents of the present invention involve the covalent binding of an arylboronic acid tagging or labelling reagent to the imidazole of Histidine in a polypeptide (see FIG. 2—though the Figure shows a peptide comprising a hexahistidine, the presence of multiple histidines is not required according to the present invention for tagging by reaction with an arylboronic group).

Figure 1:
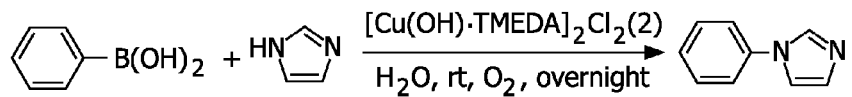
FIG. 1 shows the reaction of arylboronic acid with imidazole in the presence of a copper catalyst in accordance with Collman et al. cited above.

The reaction of arylboronic acids with imidazole in aqueous conditions at pH values between 4.6 and 9.0 in the presence of a copper catalyst, e.g. $[Cu(OH)TMEDA]_2Cl_2$, is disclosed in Collman e al. (2001), *J. Org. Chem.* 66, 1528-1531 and schematically shown in FIG. 1. However in view of the application of the present invention the reaction is typically performed at pH values below 8 to avoid reaction of the tagging or labelling reagent with glycosylated polypeptides. Although, in the methods of the present invention, the contacting of the arylboronic tagging or labelling reagent with the protein sample is typically performed in aqueous conditions, the reaction can also be performed in the presence of organic solvents or even completely in organic solvents such as $CH_2Cl_2$ as disclosed in Collman et al. (2001) *J. Org. Chem.* 66, 7892-7897.

Accordingly, a further aspect of the invention relates to the use of tagging reagents having a general structure corresponding to formula (I) described above, for the covalent tagging of Histidine-comprising peptides.

More specifically, the present invention provides methods for covalently attaching an affinity tag to a protein comprising a Histidine, comprising the step of contacting the protein with a compound with the general structure (I):

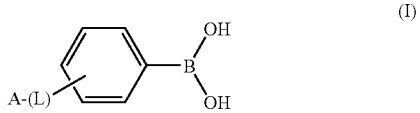

(I)

wherein A is an affinity tag and L is an optional linker, in the presence of a copper catalyst.

Specific embodiments of the invention provide methods for isolating Histidine-comprising peptides from a protein sample comprising the steps of cleaving the intact proteins in the protein sample with a cleaving agent into peptides and contacting the protein sample with an arylboronic tagging reagent having the general structural formula (I), described above, in the presence of a copper catalyst, so as to allow reaction of the arylboronic tagging reagent with Histidine where present in the peptides. The tagged peptides are then bound to an affinity matrix via the affinity tag, and the bound tagged peptides are removed from the affinity matrix to obtain the isolated peptides. Specific embodiments of the methods of the present invention involve the use of specific tagging reagents described herein, and where appropriate, the removal of the bound peptides to an affinity method using appropriate methods, depending on the nature of the affinity tag and whether or not it is connected within the tagging reagent and on the peptide with a cleavable bond, as detailed above.

Yet another aspect of the invention relates to the use of labelling reagents of the present invention in the simultaneous Mass spectrometry analysis of different protein samples. Simultaneous analysis of samples avoids the technical variability in the analysis methods.

Accordingly, the methods and tools of this aspect of the invention are of particular interest in the analysis of one or a set of two or more samples for which a comparable analysis is required. Such a set of samples can be, but is not limited to, samples from a patient taken at different time points, samples of different clinical versions of a disease, samples of different patients etc. The present invention thus provides methods and tools for identifying markers of disease progression, for differential diagnosis, and moreover for multiplex analysis in biochemical or physiological assays.

According to this aspect of the invention methods and assays are provided, wherein two or more samples are labelled using the labelling reagents of the present invention, to allow simultaneous analysis with MS.

The methods according to this aspect of the invention comprise a labelling step wherein each sample is labelled on Histidine with one (of a set) of labelling reagents, by contacting the protein with a compound with the general structure (I), described above comprises a label component, in the presence of a copper catalyst. The set of labelling reagents used in the methods of the present invention have the same or essentially the same chemical structure. More particularly, they comprise, as a label component, an isotopic or an isobaric label component.

In the methods according to this aspect of the present invention, further to the labelling step using the labelling reagents of the present invention, which results in a differential labelling of proteins in each of the samples, the different samples are pooled. By pooling of the different samples a polypeptide sample mix is obtained. This allows the immediate comparison of the different samples in the analysis.

In the steps following the labelling, the labelled peptides are isolated and analysed. Most commonly, the samples will be pooled prior to isolation of the peptides. However, it can be envisaged that pooling of the samples is performed after one or more purification or isolation steps.

As detailed below, the individual samples or pooled sample mix is typically subjected to a peptide separation step, to allow the analysis of the individual peptides on MS. Accordingly, where the methods comprise the step of labelling two or more samples with isotopic or isobaric labelling reagents according to the present invention, the chemical structure of the resulting isobaric or isotopic labels on the peptides is the same or is essentially the same for all reagents within one set of labelling reagents, such that the labels as present on the peptides will not generate a significant difference in properties in (multi-dimensional) chromatography techniques, between identical peptides that are differently labelled. Accordingly, peptides with the same amino acid sequence which are differentially labelled will have the same behaviour in these separation methods. Where differentially labelled samples have been pooled, differentially labelled identical peptides are separated together.

The methods and tools of the present invention relate to the analysis of protein samples. The term 'sample' as used herein is not intended to necessarily include or exclude any processing steps prior to the performing of the methods of the invention. The samples can be rough unprocessed samples, extracted protein fractions, purified protein fractions etc. . . . . According to one embodiment the protein samples are preprocessed by immunodepletion of abundant proteins.

Protein samples which are suitable for analysis with the tagging or labelling reagents and methods of the present invention include samples of viral, prokaryote, bacterial, eukaryote, fungal, yeast, vegetal, invertebrate, vertebrate, mammalian and human origin. The preparation of samples differs depending on the organism, tissue or organ investigated, but standard procedures are usually available and known to the expert. With respect to mammalian and human protein samples it covers the isolation of cultured cells, laser micro-dissected cells, body tissue, body fluids, or other relevant samples of interest. With respect to the fractionation of proteins in a sample, cell lysis is the first step in cell fractionation and protein purification. Many techniques are available for the disruption of cells, including physical, enzymatic and detergent-based methods. Historically, physical lysis has been the method of choice for cell disruption; (homogenisation, osmotic lysis, ultrasound cell disruption) however, it often requires expensive, cumbersome equipment and involves protocols that is sometimes difficult to repeat due to variability in the apparatus (such as loose-fitting compared with tight-fitting homogenisation pestles). In recent years, detergent-based lysis (using e.g. Poppers Reagens (Pierce Chemicals)) has become very popular due to ease of use, low cost and efficient protocols.

Mammalian cells have a plasma membrane, a protein-lipid bilayer that forms a barrier separating cell contents from the extracellular environment. Lipids comprising the plasma membrane are amphipathic, having hydrophilic and hydrophobic moieties that associate spontaneously to form a closed bimolecular sheet. Membrane proteins are embedded in the lipid bilayer, held in place by one or more domains spanning the hydrophobic core. In addition, peripheral proteins bind the inner or outer surface of the bilayer through interactions with integral membrane proteins or with polar lipid head groups. The nature of the lipid and protein content varies with cell type. Clearly, the technique chosen for the disruption of cells, whether physical or detergent-based, must take into consideration the origin of the cells or tissues being examined and the inherent ease or difficulty in disrupting their outer layer(s). In addition, the method must be compatible with the amount of material to be processed and the intended downstream applications.

In particular embodiments, protein extraction also includes the pre-fractionation of cellular proteins originated from different compartments (such as extracellular proteins, membrane proteins, cytosolic proteins, nuclear proteins, mitochondrial proteins). Other pre-fractionation methods separate proteins on physical properties such as isoelectric point, charge and molecular weight.

According to a particular embodiment, the samples are pre-treated prior to tagging/labelling or cleavage, so as to denature the proteins for optimised access to reagents or proteases, using appropriate agents (e.g., guanidinium chloride, urea, acids (e.g. 0.1% trifluoric acid), bases (e.g. 50% pyridine) and ionic or non-ionic detergents). Cysteine residues are reduced with reducing agents such as (dithiothreitol (DTT), 2-mercaptoethanol and 2-mercaptoethylamine, and those that are phosphines and their derivatives, such as Tris (carboxyethyl) phosphine (TCEP) or Tris(2-carboxyethyl) phosphine Hydrochloride).

In specific embodiments the methods of the present invention may include one or more steps wherein one or more functional groups of amino acids (other than Histidine) are irreversibly or reversibly modified with protein modification agents, prior to the tagging or labelling methods of the invention. Examples are steps for modifying the thiol group of Cysteine, modifying the hydroxyl group of Serine and Threonine with silylating agents, acetylating the amine group of Lysine, modifying the carboxyl group of Aspartic acid and Glutamic acid. Specific examples of such modifications are detailed below:

Thiol-reactive groups react with the side chain of cysteine. Thiol-reactive groups include epoxides, alpha-haloacyl group, nitrites, sulfonated alkyl or aryl thiols, alkyl halides, aryl amides and maleimides. A particular example is iodoacetamide or a derivative thereof.

Amino-reactive groups react with the epsilon amine group of the side chain of lysine or react with the amine at the N-terminus of a polypeptide. Amino-reactive groups tag amino groups in proteins and include sulfonyl halides, isocyanates, isothiocyanantes, active esters, including tetrafluorophenyl esters, pentafluorophenyl esters, N-hydroxysuccinimidyl esters, N-hydroxysulfosuccinimidyl esters, 2-nitrophenyl esters, 4-nitrophenyl esters, 2,4-dinitrophenylesters and 2,4-dihalophenyl esters, acid halides, and acid anyhydrides and mixed anhydrides. In addition, amino reactive groups include aldehydes or ketones in the presence or absence of $NaBH_4$ or $NaCNBH_3$.

Carboxylic acid-reactive groups react with the side chains of aspartic acid and glutamic acid or react with the C-terminus of a polypeptide. Carboxylic acid reactive groups include amines or alcohols in the presence of a coupling agent such as dicyclohexylcarbodiimide, or 2,3,5,6-tetrafluorophenyl trifluoroacetate and in the presence or absence of a coupling catalyst such as 4-dimethylaminopyridine; and transition metal-diamine complexes including Cu(II) phenanthroline.

Ester reactive groups include amines which, for example, react with homoserine lactone. Methionine is converted upon homoserine lactone during CNBr cleavage.

Phosphate reactive groups react with phosphorylated amino acids such as phosphoSer, PhosphoThr and Phospho-Tyr. Phosphate reactive groups include chelated metal where the metal is, for example Fe(III) or Ga(III), chelated to, for example, nitrilotriacetiac acid or iminodiacetic acid. These agents react with posphorylated amino acids (such as phosphoserine, phosphothreonine, and phosphotyrosine).

Aldehyde or ketone reactive groups include amine plus $NaBH_4$ or $NaCNBH_3$, or these reagents after first treating a carbohydrate with periodate to generate an aldehyde or ketone.

Hydroxyl reactive groups react with serine and threonine. Hydroxyl reactive groups include trityl-halides or a silyl-halide reactive moiety which is either substituted or unsubstituted.

According to particular embodiments, the tagging and labelling methods of the invention comprise a cleaving step, whereby the proteins of the one or more protein samples are processed into peptides. This cleaving step can take place either prior to or after the tagging/labelling step. This cleaving step is generally performed to allow the analysis of smaller peptides, rather than the full-length proteins. It is easier to separate peptides than proteins on high throughput systems such as LC, and to interpret sequence data from peptides in MS/MS.

The cleaving of peptides can be achieved by different cleaving agents.

Suitable chemicals for protein cleavage include cyanogen bromide (CNBr), BNPS skatole (2-(2'-Nitrophenylsulfonyl)-3-methyl-3-Bromoindolenine), formic acid, hydroxylamine, iodobenzoic acid, NTCB+Ni (2-nitro-5-thiocyanobenzoid acid). Suitable proteolytic enzymes include Asp-N Endopeptidase, Caspase 1, 2, 3, 4, 5, 6, 7, 8, 9, or 10, Chymotrypsin; Clostripain, Enterokinase, Factor Xa, Glutamyl Endopeptidase, Granzyme B, LysC Lysyl endopeptidase, Papain, Pepsin, Proline-Endopeptidase, Proteinase K, Staphylococal peptidase I, Thermolysin, Thrombin, Trypsin.

Depending on the type of protein sample, a combination of chemical and enzymatic cleavage is performed or a double enzymatic digestion is performed.

According to a particular embodiment, the cleaving of proteins is performed using trypsin, which is the enzyme with the highest specificity (Lysine and Arginine) and efficiency. In vertebrates Lysine occurs in proteins with a frequency of 7.4% and Arginine with a frequency of 4.2%. A tryptic digest thus results in peptides with an average length of 9 amino acids. Alternatively, where lysine has been modified to no longer act as a substrate for trypsin peptides with an average length of 25 amino acids are formed by trypsin cleavage. Such peptides are well suited for chromatographic and MS techniques.

Accordingly, a particular embodiment of the present invention provides methods which comprise a tagging/labelling step prior to a cleaving step wherein the tagged/labelled proteins are digested with trypsin. According to a more particular embodiment, prior to the digestion, the labelled proteins are treated with an acetylating agent to modify the side chains of lysine before a tryptic digestion is performed. The modified Lysine will not be recognised as a substrate for trypsin. It should be taken into account, however, that non-modified cysteine residues, when reacted with an acetylating agent such as e.g. acetic acid anhydride to form homoarginine, will become a substrate of trypsin. Accordingly, further specific embodiments of these methods include a step wherein Cysteine residues are modified prior to the modification of Lysine. Additionally, it should be noted that, as a consequence of the treatment of polypeptides with an acetylating agent, the aminoterminus of the polypeptides will also be acetylated. This may be of relevance if the aminoterminus of the peptides is considered for e.g. further labelling steps (e.g. in methods involving double labelling, see below)

In the methods of the present invention, Histidine-comprising proteins present in a protein sample, which are tagged/labelled in the tagging/labelling step, but which do not comprise a protein cleavage site, will be processed as such in the remainder of the analysis as other peptides. Accordingly, proteins or peptides not comprising a Histidine, are removed from the sample in the affinity purification step of the methods of the present invention and are not taken into account in the analysis.

The tagging and/or labelling methods making use of the tagging and labelling reagents described herein are typically of use in the context of the analysis of protein samples using MS. Analysis of protein samples using MS typically requires, prior to the actual MS, the purification of the individual peptides by one or more peptide separation techniques. Accordingly, where the protein samples to be analysed are complex, the methods of the present invention typically comprise one or more peptide separation steps wherein, the one sample or a pooled sample mix is subjected to one or more peptide separation techniques to selectively isolate the tagged/labelled polypeptides or peptides from the polypeptide sample mix. Suitable separation techniques, which allow the separation of a complex protein or peptide sample into two or more, up to multiple fractions (in the context of the isolation of labelled or tagged peptides) are known to the skilled person and include, but are not limited to isoelectric focusing, SDS PAGE, 2-dimensional gel electrophoresis, size-exclusion chromatography, ion exchange chromatography, reversed-phase HPLC, affinity chromatography, . . . etc.

When the sample consists of larger peptides (e.g. between Mr 3000 and 100.000) 2D GE can be used. For peptide samples, obtained from e.g. proteolytic digestions, 2D LC approaches are more suitable for separation, and also the automation and throughput is significantly better. Several technologies to separate protein/peptide digests by liquid chromatography have been described, reversed-phase (RP)-HPLC, and 2-dimensional liquid chromatography. Also capillary electrophoresis (CE) is a method suitable for the separation of peptides.

2D-LC generally uses ion-exchange columns (usually, strong cation exchange, SCX) on-line coupled with a reversed phase column, operated in a series of cycles. In each cycle the salt concentration is increased in the ion-exchange column, in order to elute peptides according to their ionic charge into the reversed phase system. Herein, the peptides are separated on hydrophobicity by e.g. a gradient with $CH_3CN$.

Many parameters influence the resolution power and subsequently the number of proteins that can be displayed by LC-MS. Usually, the 'on-line' configuration between the first-dimension separation technique (SCX) and the second-dimension RP-HPLC separation approach is set up for sample fractionation. Ion exchange chromatography can be performed by stepwise elution with increasing salt concentration or by a gradient of salt. Typically, SCX is performed in the presence of, e.g. up to 30% acetonitrile, to minimise hydrophobic interactions during SCX chromatography. Prior to Reversed Phase chromatography on e.g. a C18 column, organic solvents such as acetonitrile are removed, or strongly reduced by e.g. evaporation.

The tagging and labelling methods of the present invention are hereafter illustrated by the following exemplary schemes.

One embodiment of the methods of the present invention is illustrated by FIG. 3, wherein the tagging of a protein sample using a boronic acid tagging reagent with a biotin affinity tag connected via a linker comprising a disulfide is exemplified.

In a first step, the proteins in a cell lysate are denatured, and Cysteines are modified by carboxymethylation with iodoacetamide. In a next step the proteins are cleaved into peptides with trypsin. Thereafter the peptides with Histidine are labelled with a Histidine reactive tagging reagent. The tagged peptides are bound to a matrix with avidin as capture reagent, to which Histidine tagged peptides bind. After removal of the unbound peptides, the peptides are removed from the affinity matrix with a reducing agent (e.g. dithiothreitol) which cleaves the peptide from the bound affinity tag. The eluted peptides are subsequently separated by one- or two-dimensional chromatography and analysed by MS.

A further embodiment of the methods of the present invention is illustrated in FIG. 4. The labelling scheme illustrated by FIG. 4 involves the labelling of 4 protein samples using labelling reagents according to the present invention, comprising a protein reactive group (PRG) which is a Histidine reactive group as described herein.

In a pre-processing step the samples are denatured, reduced and subsequently all Cysteines are modified by carboxymethylation and the amine of all Lysines are modified. The different steps of the labelling scheme comprise:

The 4 protein samples are each labelled with one of a set of labelling reagents according to an embodiment of the present invention, wherein each labelling reagent has a different isotopic label component, and whereby the labelling reagents comprise a biotin affinity tag which is connected to the PRG via a linker comprising a disulfide group.

After the labelling, all samples are pooled and treated as one reaction mixture which decreases variations due to the manipulation of individual samples.

The Histidine-labelled pooled sample mix so obtained is digested with trypsin.

To reduce the number of peptides for further analysis, the labelled peptides are isolated via the biotin affinity tag introduced by the labelling reagent on the peptides. This is done using (strept)avidin affinity techniques. The affinity tag is removed from the labelled peptides by incubating them in reducing conditions.

After the affinity step, each of the isolated peptide comprises a modified Histidine and carries an isotopic label. Consequently, every peptide is informative upon analysis via MS. The method further includes the following steps wherein:

The pooled peptides are separated by e.g. liquid chromatography. Herein peptides that are identical but which originate from a different sample and are thus differently labelled behave in an essentially identical manner. Despite the different isotopic labels which are present on identical peptides originating from a different sample, this will not affect their elution as the different labels in each label set have the same chemical formula or essentially the same chemical formula.

Each separated peptide fraction is analysed by MS, which should generate four signals, with a different mass, corresponding to the presence of a "lighter" or a "heavier" isotopic label component.

The particular embodiment of methods of the invention illustrated above uses a set of labelling reagents with 4 different isotopic labels. A higher number of samples can be analysed simultaneously when a set of labelling reagents is used wherein a higher number of combinations of different isotopes is possible. Alternatively, use can be made of isobaric labelling reagents.

The above-described exemplary labelling protocol is suitable for determining e.g. differences in expression level of individual proteins in different samples. Different alternative protocols are envisaged, depending on particular applications.

The methods of the present invention are useful for the detection of biomarkers, e.g. in the context of disease. When comparing samples of disease (e.g. disease vs. control), depending on the sample, a large number of proteins are present and thus a large number of peptides have to be analysed by MS and MS/MS. This amount can be as high as several hundreds or even more than thousand. For many of them however, the presence and relative amount will be the same in the different samples. However, significant differences in the presence and relative amount in different samples can be observed for a limited number of peptides which are correlated with a condition of the disease.

Analysis of the Histidine-comprising peptides obtained from these samples makes it possible, either by sequence analysis or, as described below, by comparison with a database, to determine the protein from which the peptide originates. The analysis will be even more reliable when it is observed that, for different peptides from a same protein, an identical expression level is detected.

It will be appreciated that the labelling methods of the present invention are applicable in proteomics, protein expression profiling, biomarker discovery and target discovery.

High multiplexing as obtained with some embodiments of the methods of the present invention allows analysing a number of different conditions in one single experiment. The method is particularly useful for studying the expression profile of a sample obtained from different disease states. Samples which are analysed are derived from one or more of a healthy person, a person with a benign disorder, a person with a malignant disorder (mild or aggressive), from persons responding or not responding to a treatment, from persons having a disorder which manifests in different parts of the body, from persons before during and after treatment, from persons receiving a different method of treatment and from otherwise healthy persons having one or more symptoms of a disorder. Disorders which are considered in the context of the present invention include bacterial or viral infections, immunological disorders, cardiovascular disorders and cancer.

The above embodiments illustrate the most straightforward application of the tagging and labelling reagents and exemplary methods of use thereof provided by the present invention. It should be noted that the tagging and labelling reagents of the present invention can also be used in more complex applications, e.g. in combination with other labelling reagents which ensure labelling through a functional group of the peptide which is different from Histidine, more particularly the amino or carboxyl groups at the N- or the C-terminus of peptides after cleavage. Accordingly, the present invention also envisages methods wherein peptides of a protein sample are tagged using the tagging reagents of the present invention and, in a labelling step which can take place either prior to or after the tagging step, are reacted with a reagent such as e.g. The Histidine specific labelling reagents of the present invention are also suitable for double labelling methods, wherein a first labelling is performed on Histidine with a labelling reagent of the present invention and a second labelling is performed on a another functional group in a protein or a peptide. According to one embodiment, proteins in a sample are first labelled on Histidine, whereafter the proteins are cleaved. The cleaved peptides are then labelled on either the N-terminus or the C-terminus (i.e. functional groups which are present on all cleaved peptides). The isolation of the Histidine-comprising peptides can be performed before or after the second labelling step. According to another embodiment, proteins in a sample are first cleaved whereafter the N-terminus or the C-terminus is labelled. Hereafter, these labelled peptides are further labelled on Histidine with the labelling reagents of the present invention. Thereafter the double labelled peptides are isolated by affinity purification.

In the double labelling methods described above, the nature of the second labelling reagent will be dependent on the nature of the labelling reagent according to the present invention used (or visa versa). Typically a combination of isobaric and isotopic reagents is used, whereby the Histidine-reactive labelling reagents of the present invention can have either an isotopic label or an isobaric label component. In a very particular embodiment, one labelling is performed with a Histidine reactive labelling reagent comprising an isobaric label while the other labelling is performed by protease (e.g. trypsin) mediated incorporation of one or two $^{18}O$ isotopes at the C-terminus of cleaved peptides. Protease mediated $^{18}O$ labelling is performed as described in Heller et al. (2003) *J. Am. Soc. Mass Spectrom.* 14(7), 704-718 and Schnolzer et al. (1996) *Electrophoresis* 17, 945-953.

A further aspect of the present invention provides methods for identifying proteins in a sample, based on the selective tagging and isolation of Histidine-comprising peptides as described for the tagging reagents above, the determination of the mass of the tagged Histidine-comprising peptides and the identification of the isolated Histidine comprising peptides, based on the comparison with a database of Histidine-comprising peptides. More specifically the identification methods of the present invention involve the cleaving of proteins of a sample into peptides, the selective tagging of Histidine-comprising peptides using the arylboronic acid tagging reagents of the present invention, followed by the selective isolation thereof, and, further to purification, the determination of the mass of the isolated His-containing peptides and the comparison of this mass and optionally one or more other physiochemical properties. of the isolated His-containing peptides with a database of His-containing peptides. Accordingly, this aspect of the present invention relates to determining the mass by MS of purified Histidine-comprising peptides from a mixture and identifying the peptide by comparing the identified mass with a database of masses. The methods of the present invention allow the identification of Histidine-comprising peptides (and their corresponding parent protein, accordingly), with high accuracy without the need for de novo sequence determination on MS/MS.

An advantage of the proposed procedure is that the Histidine-comprising peptides of all proteins are known for organisms for which their genome has been sequenced (such as man, mouse and rat but also lower organisms such as *Drosophila, C. elegans* and yeasts). The exact molecular weights of these peptides can be predicted, which can be used to support the identification of the peptide underlying a measured mass spec signal. This is particularly true for the currently available high-performance mass spectrometric techniques like FT-ICR, which can achieve resolutions on the order of >500,000 and a mass accuracy of <1 ppm.

Further, as the nature of expected Histidine comprising peptides is known from in silico analyses of genomic sequences, a library of synthetic peptides can be generated and the exact characteristics of each peptide during the preparation process (e.g., retention time on different chromatographic materials, behaviour in ESI/MALDI-TOF) can be determined and compared to identified peptides from the complex protein mixture. This significantly improves the confidence in correct protein identifications.

Accordingly, typically the database is a database comprising the mass of all Histidine-comprising peptides generated by a specific cleaving agent when cleaving the proteome of a specific organism. More specifically such a database comprises the mass of these peptides which are identified by a peptide identifier and includes information on the one or more parent proteins from which the peptide originates. Comparison of the mass of an isolated peptide with the database allows the identification of the parent protein.

It is noted that upon reaction of an arylboronic acid with a Histidine within a peptide, at least a benzyl group becomes attached to the peptide. This group absorbs UV light and increases the mass of a peptide by at least 78 for each modified Histidine. Accordingly, this change in weight (and potentially other properties) should be taken into account upon MS analysis and accordingly upon comparison with the database. Where the affinity tag is not removed, or where an additional labelling component is added, the mass of the isolated and purified tagged peptide may be further increased. Optionally the masses provided in the database can be corrected for the presence of a benzyl group with or without a tag or label for each Histidine present therein.

According to the present invention, the identification of proteins within a sample optionally includes taking into account one or more other physiochemical properties of the Histidine-comprising peptides. Optionally, where the mass of the isolated peptide corresponds to more than one peptide in the database, the one or more physiochemical properties can be taken into account in the comparison, to allow the positive identification.

Typically, the methods of identifying the presence of a protein in a sample according to this aspect of the present invention comprise the steps of modifying the Histidine-comprising proteins in the protein sample by contacting the proteins with a tagging reagent with the general structure (I), described herein in the presence of a copper catalyst, so as to selectively tag all Histidines in the protein sample. The method then further comprises the step of cleaving the proteins in the protein sample into peptides with a cleaving agent, and the isolation from these generated peptides of those peptides comprising Histidine, via the affinity tag. In further steps the isolated Histidine-comprising peptides are purified by one or more peptide purification steps, so as to obtain purified Histidine-comprising peptides. Additionally, or during these peptide purification steps, at least one physicochemical property, other than the mass, of the purified Histidine-comprising peptides is determined. Alternatively the at least one additional physicochemical property can be calculated, based on information obtained during the peptide purification steps. In a next step, the mass of the isolated and purified Histidine-comprising peptides is determined on MS. Finally, for each isolated and purified Histidine-comprising peptide, the mass and the at least one other physicochemical property is compared to a database comprising the mass and one or more physicochemical properties of all Histidine-comprising peptides as described above.

In order to ensure an accurate identification of peptides using the database the theoretical cleavage pattern of a sample by a cleaving agent should correspond as closely as possible to the experimental situation. For example, it may be necessary to take into account that the use of CNBr for cleaving C-terminally of Methionine can also result in the cleavage C-terminally of Tryptophane. Chymotrypsin which cleaves preferentially C-terminally of aromatic amino acids will also cleave C-terminally of other hydrophobic amino acids, depending on the incubation time and the concentration of enzyme in the sample.

Also, in order to allow a definite identification of peptides using a database (i.e. in order for the database to include a maximal number of different peptides and a minimal number of identical peptides originating from a different parent protein), the average size of the generated peptides is of importance. The shorter the peptides, the greater the chance that peptides from different proteins will have the same mass and even have the same sequence and will behave in an identical way in purification and analysis method. Accordingly, depending on the nature and complexity of the sample, an enzyme with a less commonly occurring cleavage site may be preferred.

Optionally the identification methods of the present invention include the analysis of control peptides either during the analysis of the sample (internal control) or in a test run.

In this embodiment, one or more up to a library of synthetic Histidine-containing peptides is generated and the exact characteristics of each peptide during the preparation process (e.g., retention time on different chromatographic materials, behaviour in ESI/MALDI-TOF) is determined. Where the peptides generated are identical to specific peptides generated from a protein sample, the information generated for the synthetic peptides can be used to compare to the data obtained for the natural peptides. This is expected to significantly improve the confidence in correct identification.

As described in the context of the tagging and labelling methods above, particular embodiments of the identification methods of the present invention involve a cleavage step using trypsin, in view of its high specificity and efficiency. Alternatively, where cleavage at both Lys and Arg results in peptides which are too short, other enzymes can be used such as endoproteinase Arg-C (Arginine specific), endoproteinase Lys-C (Lysine specific), *S. aureus* V8 protease (Asp/Glu specific). Alternatively, as described above, side chains of Lysine are modified by acetylation to limit tryptic cleavage to Arginine residues (and optionally unmodified cysteine which is acetylated into homoarginine and becomes a substrate for trypsin, see above).

The identification methods of the present invention comprise an identification step, which is based on comparing data on the physicochemical characteristics of the peptides with those of a database of peptides.

Accordingly, for each peptide fraction obtained in the one or more separation steps of the methods of the present invention, data are collected and stored relating to the behaviour of the peptide in the separation method, e.g. during chromatography. Such data include for instance the pH at which the purification was performed, the percentage of organic solvent at which a peptide elutes from a reversed phase column, the salt concentration at a given pH at which a peptide elutes from an ion exchange matrix, the binding (or not binding) of the peptide to a certain resin at a given pH etc. . . .

Additionally or alternatively, further data can be collected for each peptide, which is not directly obtained from the peptide separation and purification step(s) in the methods of the present invention. Accordingly, for each peptide, a fraction of the isolated peptide can be stored to perform assays to determine properties which are not determined during purification. Such assays for example include determination of the solubility, partition coefficient in water/organic solvent systems, detection of specific amino acids side groups (e.g. —OH, —SH, —NH2), etc.

In a further step of the identification methods of the present invention, the Histidine-comprising peptide fractions which have been isolated as described above, are analysed by Mass spectrometry.

It is noted that, the identification methods of the present invention, can be used for the identification of proteins within one sample or for the identification of proteins within a pooled sample mix. In the latter case, in addition to the tagging of the Histidine-comprising proteins in the samples, the samples are differentially labelled to allow identification of the origin of the purified tagged peptides. Accordingly to a particular embodiment, differential labelling is ensured using the labelling reagents of the present invention which allow simultaneous tagging and labelling of Histidine-comprising peptides. Accordingly; where two or more samples are analysed simultaneously as a pooled sample mix, the peptide fraction potentially contains identical Histidine-comprising peptides which are differentially labelled.

The accurate determination of the mass of the Histidine-comprising peptides in MS spectra which allows comparison with an in silico database for identification is achieved by the high mass accuracy of high-resolution mass spectrometers. Mass measurements by spectrometry are performed by the ionisation of analytes into the gas phase. The mass-to-charge ratio (m/z) of the ionised molecules is determined and the number of ions for each individual m/z value is counted. Each feature in an MS spectrum is thus defined by two values, m/z and a measure on the number of ions detected.

As indicated above, in a further step of the identification methods of the present invention, the experimentally determined mass of a Histidine-comprising peptide is compared with the masses of in silico generated peptides in a database.

The mass of a peptide is correlated with its amino acid composition. Based on the mass alone however, it is not always possible to positively identify a peptide. For instance, mass alone will not allow discriminating between peptides having the same amino acid composition but a different sequence (A1-A2-A3-A4-A5 versus A5-A1-A2-A3-A4). Furthermore certain masses can correspond to a set of peptides having a different sequence. For example a short peptide with amino acids with longer side chains can have the same mass as a longer peptide which has amino acids with shorter side chains.

Using the Histidine-comprising peptide tagging and isolation as described in the present invention, the number of peptides generated from a protein sample is strongly reduced, compared to the total number of peptides generated by enzymatic digestion of the sample. Accordingly, the in silico tryptic peptide database used for the identification also needs to contain only Histidine-comprising peptides (so-called Histidine-comprising peptide database).

Existing protein and sequence databases can be used as a basis to generate a Histidine-comprising peptide database corresponding to the proteome of any organism. For an ever-increasing list of organisms, the complete genome, and the proteome deduced therefrom is known (www.ncbi.nlm.nih.gov/genomes). Thus in silico Histidine-comprising peptide databases can be generated wherein protein cleavage and peptide isolation is simulated. Depending on the efficiency of a cleaving agent, the database can contain peptides wherein the cleavage is incomplete.

In a Histidine comprising peptide database suitable in the context of this aspect of the present invention, each entry includes the name of the parent protein and the mass of the corresponding Histidine comprising peptide. For each entry, also the amino acid composition is important, to calculate mass differences caused by natural post-translational modifications (e.g. phosphorylation on Serine, Threonine and Tyrosine), treatment of the sample (e.g. deamidation of Asparagine and Glutamine) or modifications introduced during the modification/labelling of the protein and isolation of the Histidine comprising peptides, in particular the increase in mass by at least a benzene ring due to the labelling with arylboronic acids.

Nevertheless, the mass of an experimental Histidine comprising peptide can correspond to different peptides in the corresponding Histidine-comprising peptide database. For specific samples, such as samples for which little information on the expected nature of the proteins is present such database may thus not be sufficiently informative to identify the parent protein of a Histidine-comprising peptide solely on the mass of that peptide. Accordingly, specific embodiments of the identification methods of the present invention provide for an identification of the corresponding parent protein of the Histidine-comprising peptides based on not only m/z ratio, but by taking into account one or more additional characteristics such as length (number of amino acids), amino acid sequence, weight, hydrophobicity, isoelectric point, etc.

According to a particular embodiment of the invention, the database of Histidine-comprising peptides corresponds to the proteome of a specific cleaving agent, and this for a given species, corresponding to the origin of the samples. Such a peptide database also includes annotated splice variants. The in silico peptide database used in the methods of the present invention, includes calculated characteristics of Histidine-comprising peptides like length in amino acids, amino acid sequence, molecular weight, hydrophobicity, isoelectric point, etc.

It has to be considered that proteins coming from in vivo sources are often post-translationally modified, e.g., through acetyl groups, formyl groups, or pyroglutamic acid residues, all of which will have an influence on the determined m/z in a mass spectrum). Accordingly, in one embodiment of the present invention synthetic Histidine-comprising peptides are used as reference standards to validate the in silico calculated peptide characteristics.

The information from the synthetic peptide libraries is used to facilitate the identification of the nature of mass spectrometry peptide peaks, thereby optionally obviating de novo sequencing. The identification will be based on measured characteristics like HPLC retention time, isoelectric point and mass spec m/z value compared to available information stored in the in silico peptide library.

Different types of physicochemical data are considered, which, in combination with the m/z data of the Histidine comprising peptides optionally allow a further positive identification of the parent protein upon comparison with a database according to the methods of the present invention.

One type of data envisaged is data which are predicted from the sequence information and/or which can be measured during peptide purification steps and MS, such as isoelectric point, net charge at different pH values, hypothetical retention time on RP HPLC, UV absorption at 214 and 280 nm, tendency to elute from ion exchange columns at given pH and salt concentrations, hydrophobicity, hydrophilicity.

Hydrophobicity can be calculated for example by the algorithm of Bull and Breese. (1974) *Arch. Biochem. Biophys.* 161, 665-670. Isoelectric points can be calculated for example on www.expasy.ch/tools/pi_tool.html. Retention times on reverse phase columns are for example predicted according to the method of Krohkin et al. (2004) *Mol. Cell. Proteomics* 3, 908-919.

Additionally or alternatively, the database used in the context of the identification methods of the present invention comprises data obtained in additional experiments and not directly derived from peptide purification, such as, but not limited to, data on solubility, partition over water/organic solvent two phase systems, assays for the detection of protein reactive groups (OH, $NH_2$, SH), ionisation potential, dipole moment, hydrogen bonding capacity and ion mobility in gas phase.

Accordingly, the methods of the present invention which provide an identification based on a comparison with an "annotated" Histidine-comprising peptide database (i.e. comprising additional physicochemical characteristics which can be used for identification purposes), allow identification of the corresponding parent protein with increased accuracy.

Optionally and additionally or alternatively to the additional physicochemical parameters described above, the Histidine-comprising peptide database used in the context of the present invention further comprises information on expression patterns of the parent protein, etc., which further help to identify the parent protein. Where the parent proteins differ in amino acid sequence except for a conserved peptide sequence which happens to be the only sequence comprising a Histidine within the protein, the corresponding entries for these peptides in the annotated Histidine-comprising peptide database will indicate Histidine-comprising peptides with identical mass and identical physicochemical properties. The further annotation of these entries with details on possible differential expression of the parent proteins during development of the organism, or tissue specific expression, can nevertheless allow the assigning of the correct parent protein to the isolated Histidine-comprising peptide. Indeed, depending on the origin of the protein sample, it may be possible to select from the different possible parent proteins, one of which the expression matches with that of the sample.

In the identification methods of the present invention, for each peptide the mass is determined and compared to the annotated Histidine-comprising peptide database. Accordingly, those database entries are selected that have a calculated mass which corresponds to the measured mass of the isolated peptide. Depending of the MS apparatus and the type of sample, comparison is performed with the monoisotopic mass or with the average mass.

When the monoisotopic mass is used, typically a measuring error of 0.1 mass units is included to select entries from the database. When average mass is used typically a measuring error of 1 Da is included to select entries from the database. When the measured mass corresponds with only one entry in the database, the parent protein is immediately identified.

According to particular embodiments, when the measured mass corresponds to more than one entry in the database, all these entries are selected as a subset. A further identification is performed based on the comparison of the physicochemical parameters of the isolated peptides with those for the subset of entries in the database. Typically, those physicochemical parameters that can be directly derived from the peptide purification steps are considered first. According to a particular embodiment, at least three physiochemical characteristics are considered and identification is performed based on a "best fit" analysis. When only one additional parameter is considered, which parameter is chosen largely depends on the discriminating power of that parameter within the set of peptides in the Histidine comprising database with the same mass. For example if the different peptides in the Histidine-comprising peptide database with a mass corresponding to the experimentally determined mass of a peptide have differing amounts of aromatic amino acids, the UV absorption at 214 and 280 nm can be used as a selection criterion. However, it should be noted that by using the arylboronic acid tagging or labelling reagents of the present invention, an aromatic ring is incorporated in each Histidine comprising peptide. If in another example, in a set of 3 peptides in the database with the same m/z ratio, these all have the same net charge, but the distribution of the charge is different (e.g. one peptide has no charged amino acids, another has one Arg and one Asp, and another has two Arg and two Asp), the behaviour on ion exchange can be used as a criterion to correlate the isolated peptide with one specific peptide in the subset of the database.

A further aspect of the present invention provides tools and devices for the analysis of either a single protein sample or the simultaneous identification and/or quantitation of proteins in different samples. As detailed above, particular embodiments of the methods of the present invention involve the analysing of the relative occurrence of isolated, labelled polypeptides or peptides by Mass spectroscopy, followed by the identification of peptides.

Accordingly, the devices for performing the methods of the present invention comprise one or more mass spectrometric instruments.

Mass measurements by spectrometry are performed by the ionisation of analytes into the gas phase. A typical mass spectrometric instrument consists of 3 components: an ion source in order to generate ions from the molecules of interest, a mass analyser, which determines the mass-to-charge ratio (m/z) of the ionised molecules, and a detector that registers and counts the number of ions for each individual m/z value. Each feature in an MS spectrum is defined by two values, m/z and a measure on the number of ions, which reached the detector of the instrument.

The ionisation of proteins or peptides for mass analysis in a spectrometer is usually performed by Electro-spray ionisation (ESI) or matrix-assisted laser desorption/ionisation (MALDI).

During the ESI process analytes are directly ionised out of solution and ESI is therefore often directly coupled to liquid-chromatographic separation tools (e.g., reversed phase HPLC). MALDI vaporises via laser pulses dry samples mixed with small organic molecules that absorb the laser energy like cinnamic acid to make the process more effective.

The mass analyser is a key component of the mass spectrometer; important parameters are sensitivity, resolution, and mass accuracy. There are five basic types of mass analysers currently used in proteomics. These include the ion trap, time-of-flight (TOF), quadrupole, Orbitrap, and Fourier transform ion cyclotron (FTICR-MS) analysers. Tandem MS or MS/MS can be performed in time (ion trap) and in place (with all hybrid instruments such as e.g. LTQ-FTICR, LTQ-Orbitrap, Q-TOF, TOF-TOF, triple quad and hybrid triple quadrupole/linear ion trap (QTRAP))

The analysis of protein samples using the tagging methods of the present invention optionally involve the further identification of the generated peptides by MS/MS. Alternatively, the identification methods of the present invention based on comparison with a database can be used to avoid MS/MS analysis.

Where the methods of the invention involve the analysis of a pooled mix of isotopically labelled peptides, the spectrum generated on mass spectrometer for one such labelled peptide which has been isolated from the mix of isolated labelled peptides, contains a set of peaks with the characteristic mass differences between the different isotopic label components with which the peptides have been differentially labelled (the number of peaks will be less if a protein wherein this polypeptide occurs is not expressed at all in one of the samples). Alternatively, where the label components used in the differential labelling are isobaric, a single peak is generated on MS. By subjecting this peak to CID in MS/MS, the corresponding peptides with identical mass are further fractionated to release the reporter group of the isobaric label component for identification of the presence of the corresponding differently labelled peptides. Based on Mr of the polypeptide, the amino acid composition or the amino acid sequence, the identity of the individual peptides is determined.

Devices suitable for performing the methods of the present invention optionally contain or are connected to one or more suitable separation instruments, such as electrophoresis instruments, chromatography instruments, such as, but not limited to capillary electrophoresis (CE) instruments, reversed-phase (RP)-HPLC instruments, and/or 2-dimensional liquid chromatography instruments, . . . etc.

As detailed above, the methods of the present invention optionally comprise a pre-treatment of the samples, which can be performed in a pre-treatment step comprising one or more of the sample preparation methods listed above. Accordingly, devices suitable for the methods of the present invention optionally comprise a sample preparation unit comprising one or more devices suitable for sample preparation e.g. sonication devices, chromatography systems (affinity, gelfiltration), ultrafiltration units, centrifuges, temperature controlled reaction vials with delivery systems for buffers, enzymes, detergents etc. . . .

A specific embodiment of this aspect of the invention relates to a device for single or multiplex analysis of protein samples (100) comprising one or more sample sources (101), a tagging/labelling unit (103), with corresponding tagging/label sources (104), a protein cleavage unit (105), an affinity separation unit (106), a peptide separation unit (107), a mass spectrometer unit (109) and a control circuitry and data analysis unit (110). In particular embodiments separation unit (107) comprises two consecutively linked separation systems (1107) and (2107), wherein the first separation system (1107) is e.g. a 2D gel electrophoresis system or a cation exchange chromatography system and separation system, and the second separation system (2107) is typically a HPLC reversed phase system. Mass spectrometer element (109) is an MS or MS/MS spectrometer which separates isotopic forms. using MS/MS de novo enables de novo peptide sequencing and the differential detection of reporter groups of isobaric labels, where used. MS/MS analysis can be done using 2 fundamentally different instruments. In the first type of instrument, the ion trap in which MS/MS analysis is done in the same ion trap where MS is performed, but MS/MS is done in time (trap is filled, all ions are ejected except ion(s) of interest and CID is performed and the fragment ions are scanned. Other suitable methods to fragment peptides include CAD (collisionally activated dissociation), ETD (electron transfer dissociation), ECD (electron capture dissociation), IRMPD (infrared multiphoton dissociation) and BIRD (blackbody infrared radiative dissociation).

The second type of instruments, hybrid instruments (triple quad, q-tof, ltq-ftms, ltq-orbitrap), separate MS/MS in place. e.g. parent selection is done in the first mass analyser and fragments are scanned in the second mass analyser.

The device can further comprise a number of optional elements such as a sample preparation unit (102) wherein e.g. sample lysis and immunodepletion takes place or additional protein/peptide modification units with corresponding modification reagent sources. Suitable units for incorporation into the devices of the present invention as mass spectrometer units and separation units are described above.

The device can further comprise an analysis unit (108) wherein one or more physicochemical properties of a purified peptide are determined. Data on the experimental mass of a peptide and its physicochemical properties obtained during purification and optionally obtained in the analysis unit are compared with an annotated database of C-terminal peptides (112) (indicated by dotted lines in FIG. 5).

It will be appreciated that the tagging and labelling reagents and methods of the present invention are applicable in proteomics, protein expression profiling, biomarker discovery and target discovery.

Other arrangements of the systems and methods embodying the invention will be obvious for those skilled in the art.

It is to be understood that although preferred embodiments, specific constructions and configurations, as well as materials, have been discussed herein for devices according to the present invention, various changes or modifications in form and detail may be made without departing from the scope and spirit of this invention.

EXAMPLES

Example 1

Synthesis of Boronic-Acid-Modified Biotin a: sNHS-biotin+m-APBA

500 µl of a 10 mM sNHS-biotin (sulfo-N-hydroxysuccinimido-biotin) solution, 25 µl of a 10 mM m-APBA (m-aminohenylboronic acid) solution, 60 µl of 10×PBS stock solution and 60 µl water are mixed at room temperature for two hours.

The reaction scheme is illustrated in FIG. 6. FIG. 7 shows IR spectra of the reactants sulfo-NHS-biotin (top) and m-aminophenylboronic acid (middle), and the non-purified reaction mixture after stirring (bottom), comprising the reaction product (i.e. the compound with formula (II)). The bottom spectrum shows an additional vibration at about 1685 cm-1 (indicated with an arrow in FIG. 7) which can be attributed to the amide bond formed between biotin and m-aminophenylboronic acid.

b: EDC Mediated Coupling of Biotin+m-APBA

The reaction of biotin with m-APBA is performed via EDC mediated coupling is performed in accordance with the instruction of the manufacturer (Pierce Chemical, IL, USA). The reaction scheme is shown in FIG. 8.

Example 2

Coupling of Histidine-Oligopeptide to Boronic-Acid-Modified Biotin

500 μl of a 10 mM solution Boronic-acid-modified biotin as obtained in Example 1 is mixed with 250 μl of a 10 mM solution of FITC-Ahx-His$_6$ (Fluorescein isothiocyanate—6-Aminohexacarboxylic acid-hexahistidine), 25 μl of a 10 mM solution [Cu(OH)TMEDA]$_2$Cl$_2$, 90 μl of a 10×PBS stock solution and 35 μl water. The mixture is stirred overnight in oxygen atmosphere.

The reaction scheme is illustrated in FIG. 9. Though the Figure shows a peptide comprising a hexahistidine, the presence of multiple histidines is not required according to the present invention for tagging by reaction with an arylboronic group.

The invention claimed is:

1. A method of covalently attaching an affinity tag to a protein comprising a Histidine, the method comprising the step of contacting the protein with a compound with the general structure (I):

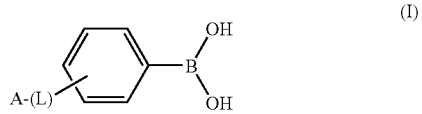

(I)

wherein A is an affinity tag, B is boron and L is an optional linker, in the presence of a copper catalyst.

2. The method according to claim 1, wherein the compound is further substituted at the aromatic ring with a halogen, an alkoxy group or an alkyl group.

3. The method according to claim 1, wherein the affinity tag A is biotin.

4. The method according to claim 1, wherein the compound corresponds to a molecule with formula (II):

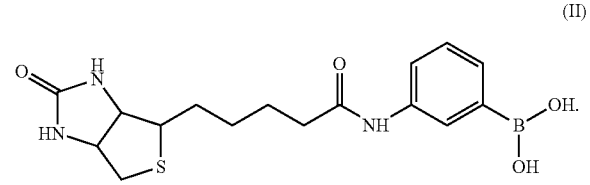

(II)

5. The method according to claim 1, wherein the compound further comprises a label.

6. The method according to claim 5, wherein the label consists of one or more heavy atom isotopes.

7. The method according to claim 1, wherein the compound corresponds to a molecule with formula (III):

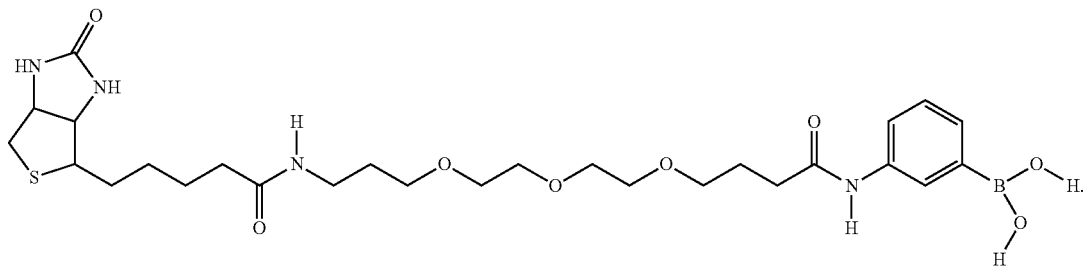

(III)

8. A method for isolating Histidine-comprising peptides from a protein sample or a mixture of pooled protein samples comprising the steps of:

a) cleaving the intact proteins in the protein sample(s) with a cleaving agent into peptides, b) contacting the protein sample(s) with an arylboronic tagging reagent having the general structural formula (I),

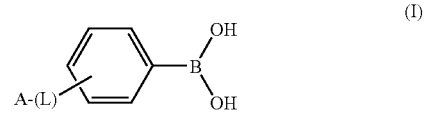

(I)

wherein A is an affinity tag, B is boron, and L is an optional linker, in the presence of a copper catalyst, so as to allow reaction of the arylboronic tagging reagent with Histidine where present in the peptides, c) binding the tagged peptides to an affinity matrix via said affinity tag, and d) removing the bound tagged peptides from the affinity matrix to obtain the isolated Histidine-comprising peptides.

9. The method according to claim 8 wherein step b) is performed before step a) and the arylboronic tagging reagent is contacted with the uncleaved proteins in the sample(s), resulting in a tagging of Histidine where present in the proteins.

10. A method for simultaneously analysing the occurrence of one or more proteins comprising Histidine in different samples, the method comprising the steps of:

a) optionally cleaving the intact proteins in the sample(s) with a cleavage agent into peptides, b) contacting each of the samples with one of a set of arylboronic acid labelling reagents in the presence of a copper catalyst, whereby the boronic acid labelling reagents have the general structural formula (I),

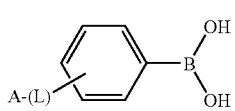

wherein A is an affinity tag, B is boron, and L is an optional linker, and further comprise a label which is an isotopic or isobaric label, such that the structure of each of the labeling reagents is essentially the same, c) pooling the different samples to obtain a polypeptide or peptide sample mix,
d) selectively isolating the labelled polypeptides or peptides from the polypeptide or peptide sample mix via the affinity tag, and
e) analysing the occurrence of the isolated labelled polypeptides or peptides by Mass Spectroscopy.

11. A method for identifying the presence of a protein in a protein sample comprising the steps of:
a) modifying Histidine of the proteins in the protein sample by contacting the proteins with a tagging reagent with the general structure (I):

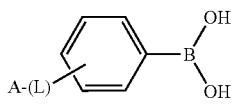

wherein A is an affinity tag, B is boron and L is an optional linker, in the presence of a copper catalyst,
b) cleaving the proteins in the protein sample into peptides with a cleavage agent,
c) isolating from said peptides the Histidine-comprising peptides, via the affinity tag,
d) purifying the isolated Histidine comprising peptides by one or more peptide purification steps, so as to obtain purified Histidine-comprising peptides,
e) determining or calculating at least one physicochemical property, other than the mass, of the purified Histidine-comprising peptides,
f) determining the mass of the isolated and purified Histidine comprising peptides on MS, and
g) comparing, for each isolated and purified Histidine-comprising peptide, the mass and the at least one other physicochemical property to a database comprising the mass and one or more physicochemical properties of all Histidine-comprising peptides generated by said cleavage agent, so as to identify the corresponding parent protein of the purified Histidine-comprising peptide, thereby identifying the presence of the parent protein in the protein sample.

12. The method of claim 11, wherein step (g) comprises identifying for each of the isolated and purified Histidine-comprising peptides, one or more Histidine-comprising peptides in the database with a mass corresponding to the mass of the isolated and purified Histidine-comprising peptide, and, when more than one peptide are identified for one isolated and purified Histidine-comprising peptide, comparing at least one other physicochemical parameter of the isolated and purified Histidine-comprising peptide with those of the more than one peptides identified in the database.

13. A compound for tagging Histidine in a protein or peptide, the compound having the general structure (I):

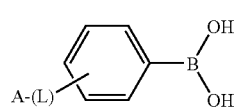

wherein A is an affinity tag selected from the group consisting of biotin or a biotin-derived molecule, maltose, a lectin, a hapten binding to hapten-specific antibodies, and glutathione, B is boron and L is an optional linker, wherein the aromatic ring is further substituted with a halogen, an alkoxy group or an alkyl group.

14. A compound for tagging Histidine in a protein or peptide, the compound having the general structure (I):

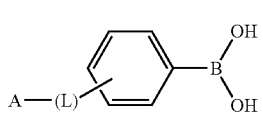

wherein A is an affinity tag selected from the group consisting of biotin or a biotin-derived molecule, maltose, a lectin, a hapten binding to hapten-specific antibodies, and glutathione, B is boron and L is an optional linker, and wherein the affinity tag A is biotin.

15. A compound for tagging Histidine in a protein or peptide, the compound having the formula (II)

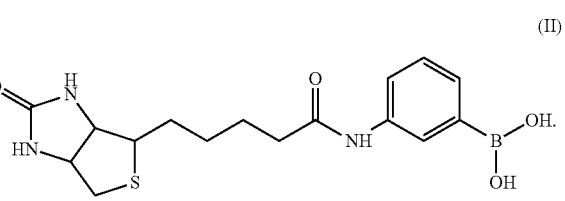

16. A compound for tagging Histidine in a protein or peptide, the compound having the general structure (I):

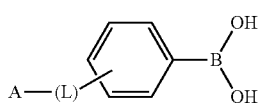

wherein A is an affinity tag selected from the group consisting of biotin or a biotin-derived molecule, maltose, a lectin, a hapten binding to hapten-specific antibodies, and glutathione, B is boron and L is an optional linker, the compound further comprising a labelling component.

17. A compound for tagging Histidine in a protein or peptide, the compound including a biotin group, an arylboronic group and having the formula (III)

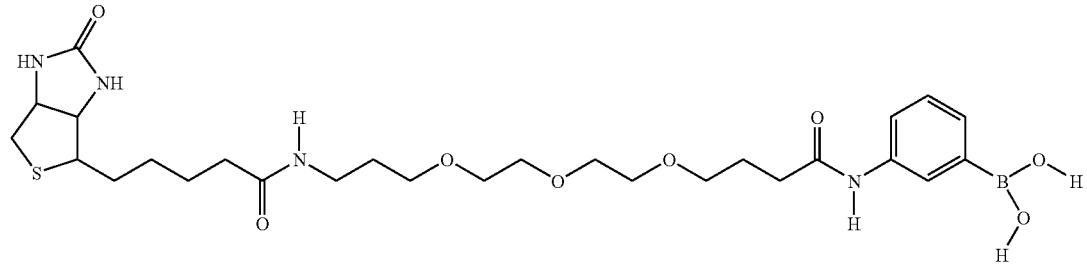

(III)

wherein one or more carbon atoms and/or one more hydrogen atoms in a linker between the biotin group and the arylboronic group includes $^{13}C$ or deuterium.

18. A set of reagents wherein individual labelling reagents of said set includes a biotin group, an arylboronic group and have a structure according to formula (III):

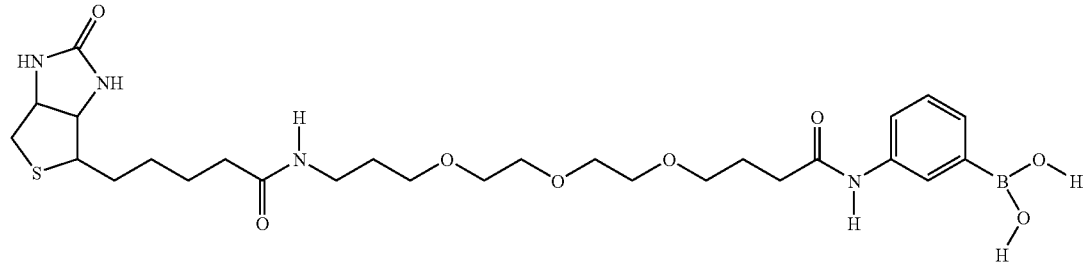

(III)

wherein one or more carbon atoms and/or one more hydrogen atoms in a linker between the biotin group and the arylboronic group includes $^{13}C$ or deuterium.

* * * * *